US012702649B2

(12) United States Patent
Zabner et al.

(10) Patent No.: US 12,702,649 B2
(45) Date of Patent: Aug. 11, 2026

(54) METHOD OF TREATING CYSTIC FIBROSIS AIRWAY DISEASE

(71) Applicant: UNIVERSITY OF IOWA RESEARCH FOUNDATION, Iowa City, IA (US)

(72) Inventors: Joseph Zabner, Iowa City, IA (US); Michael J. Welsh, Iowa City, IA (US); David A. Stoltz, Iowa City, IA (US); Mahmoud Abou Alaiwa, Iowa City, IA (US)

(73) Assignee: UNIVERSITY OF IOWA RESEARCH FOUNDATION, Iowa City, IA (US)

( * ) Notice: Subject to any disclaimer, the term of this patent is extended or adjusted under 35 U.S.C. 154(b) by 294 days.

(21) Appl. No.: 16/302,022

(22) PCT Filed: May 23, 2017

(86) PCT No.: PCT/US2017/034018
§ 371 (c)(1),
(2) Date: Nov. 15, 2018

(87) PCT Pub. No.: WO2017/205383
PCT Pub. Date: Nov. 30, 2017

(65) Prior Publication Data

US 2019/0380977 A1 Dec. 19, 2019

Related U.S. Application Data

(60) Provisional application No. 62/340,066, filed on May 23, 2016.

(51) Int. Cl.

| | |
|---|---|
| *A61K 31/133* | (2006.01) |
| *A61K 9/00* | (2006.01) |
| *A61K 33/00* | (2006.01) |
| *A61K 33/14* | (2006.01) |

(Continued)

(52) U.S. Cl.
CPC .......... *A61K 31/133* (2013.01); *A61K 9/0043* (2013.01); *A61K 33/00* (2013.01);
(Continued)

(58) Field of Classification Search
CPC .... A61K 31/133; A61K 9/0043; A61K 33/00; A61K 33/14; A61K 45/06; A61K 9/08;
(Continued)

(56) References Cited

U.S. PATENT DOCUMENTS 8,945,605 B2 * 2/2015 Boucher ................ A61M 11/06 424/434
2002/0197315 A1 * 12/2002 Haggard ................ A61K 9/167 514/19.3

(Continued)

OTHER PUBLICATIONS

Baron et al (Medical Microbiology, 4th ed., Chapter 93, Figure 93-1, 1996) (Year: 1996).*

(Continued)

*Primary Examiner* — Sahana S Kaup
*Assistant Examiner* — Amanda Michelle Petritsch
(74) *Attorney, Agent, or Firm* — Viksnins Harris Padys Malen LLP

(57) ABSTRACT

In certain embodiments, the present invention provides a method of increasing liquid pH on airway surface of a tissue in a patient in need thereof comprising administering an effective amount of a therapeutic composition comprising tromethamine to the patient.

13 Claims, 15 Drawing Sheets

(51) Int. Cl.
*A61K 45/06* (2006.01)
*A61P 11/00* (2006.01)
*A61P 31/04* (2006.01)

(52) U.S. Cl.
CPC .............. *A61K 33/14* (2013.01); *A61K 45/06* (2013.01); *A61P 11/00* (2018.01); *A61P 31/04* (2018.01)

(58) Field of Classification Search
CPC ......... A61K 47/02; A61K 31/70; A61P 11/00; A61P 31/04
See application file for complete search history.

(56) References Cited

U.S. PATENT DOCUMENTS

2008/0199410 A1* 8/2008 Johnson .................. A61P 11/00 424/663
2008/0276935 A1* 11/2008 Wang ................... A61K 31/436 128/203.15
2010/0075995 A1 3/2010 Biggadike et al.
2013/0261603 A1 10/2013 Wang
2013/0316022 A1* 11/2013 Welsh .................. A61K 31/495 424/715
2016/0175545 A1* 6/2016 Fink ...................... A61M 16/20 128/200.16

OTHER PUBLICATIONS

Chamberlin et al (https://www.atsu.edu/faculty/chamberlain/website/lectures/lecture/reairin2.htm, 2014) (Year: 2014).*

Alaiwa, M , et al., "Repurposing tromethamine as inhaled therapy to treat CF airway disease", JCI Insight 1(8), e87535 (2016).

Patent Cooperation Treaty , International Searching Authority, Search Report and Written Opinion for PCT/US2017/034018, 10 pages, Aug. 14, 2017.

* cited by examiner

Figures 5A-5C.
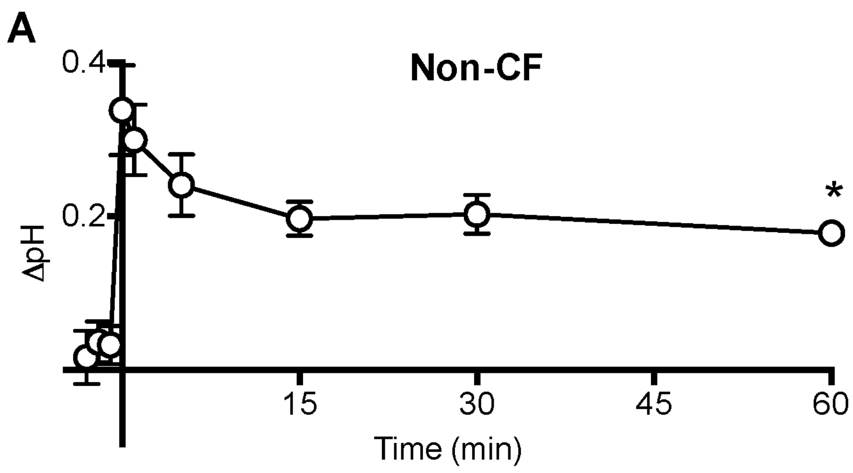
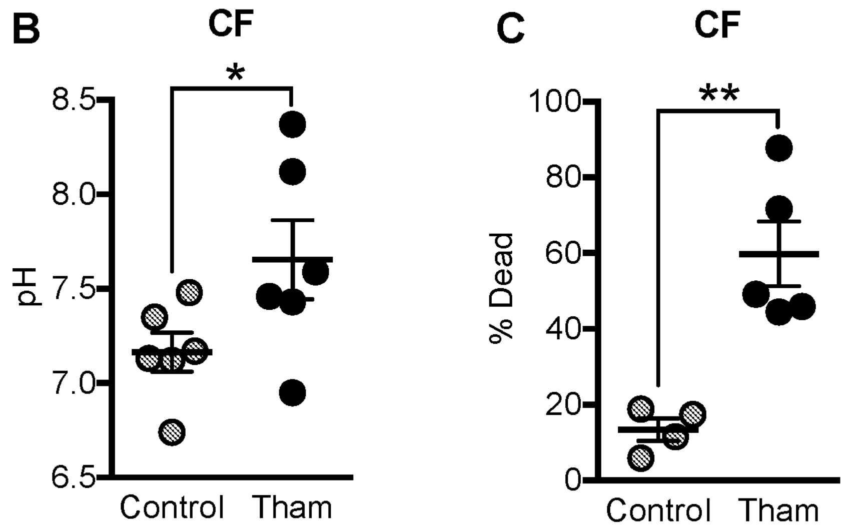

Figures 6A-6D.
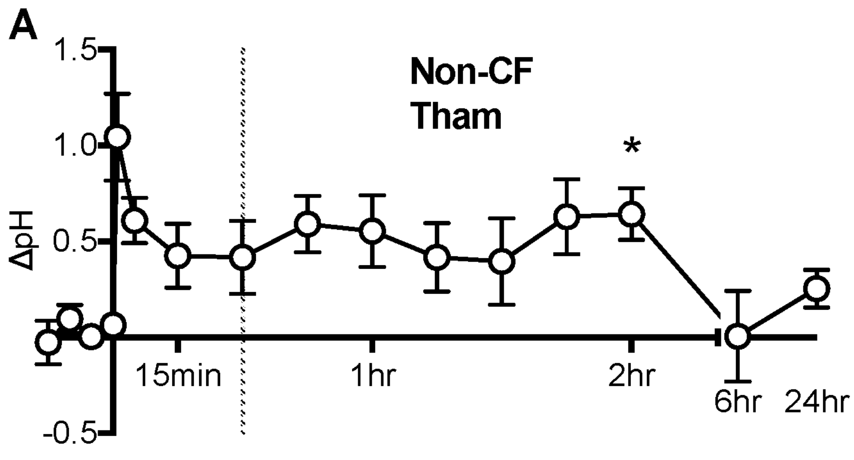
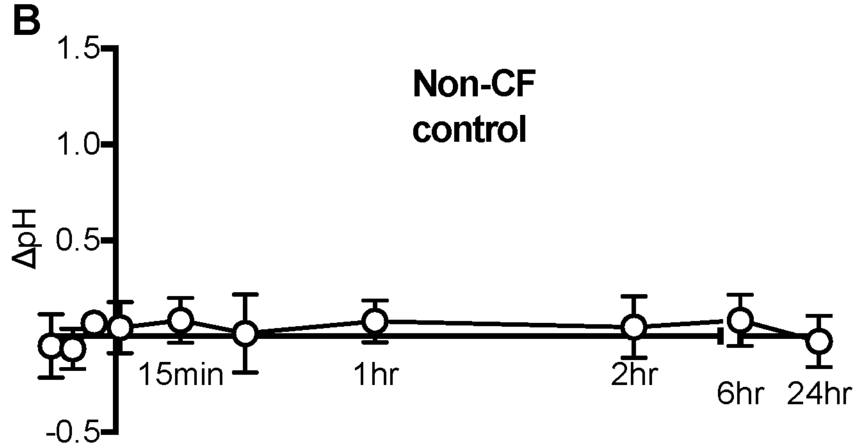
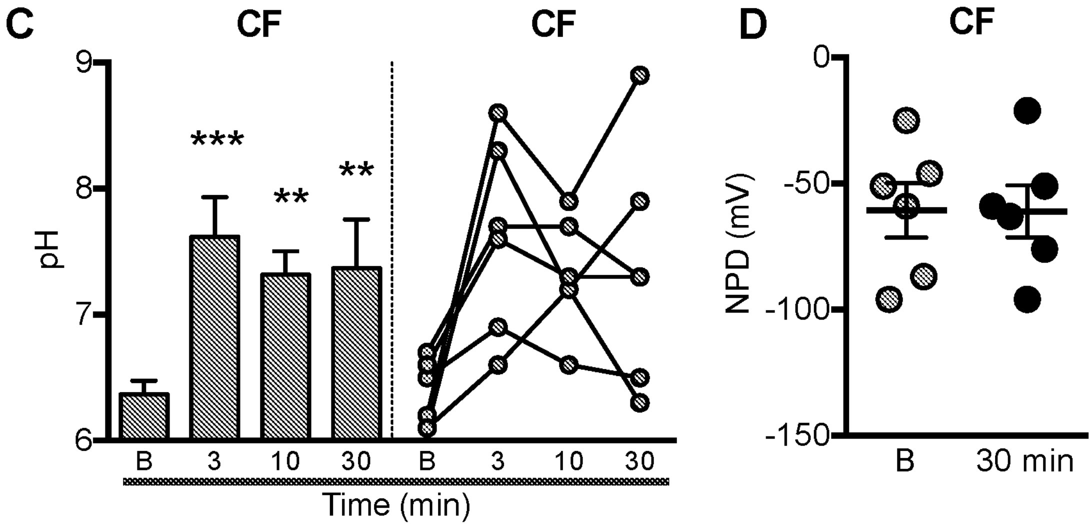

Figure 9.
| | Age | Gender | FEV1 (L) | Meds |
|---|---|---|---|---|
| Fig. 1 | | | | |
| 1 | 21 | F | 2.25 | azithromycin |
| 2 | 41 | F | 1.21 | azithromycin, colistin |
| 3 | 24 | F | 0.93 | colistin, minocycline, ciprofloxacin |
| 4 | 50 | M | 1.51 | azithromycin, tobramycin |
| 5 | 44 | M | 1.73 | azithromycin, tobramycin |
| 6 | 42 | M | 2.05 | azithromycin |
| Fig. 7 | | | | |
| 1 | 21 | F | 0.71 | azithromycin, tobramycin |
| 2 | 57 | F | 1.64 | azithromycin, cayston |
| 3 | 43 | M | 1.79 | azithromycin |
| 4 | 48 | M | 2.00 | azithromycin |
| 5 | 44 | M | 1.31 | azithromycin, colistin |
| 6 | 25 | F | 2.69 | azithromycin, tobramycin |
Figures 10A-10B
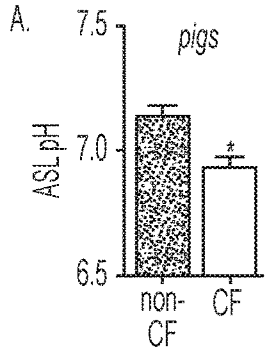
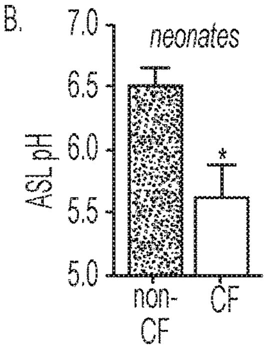

Figures 13A-13B
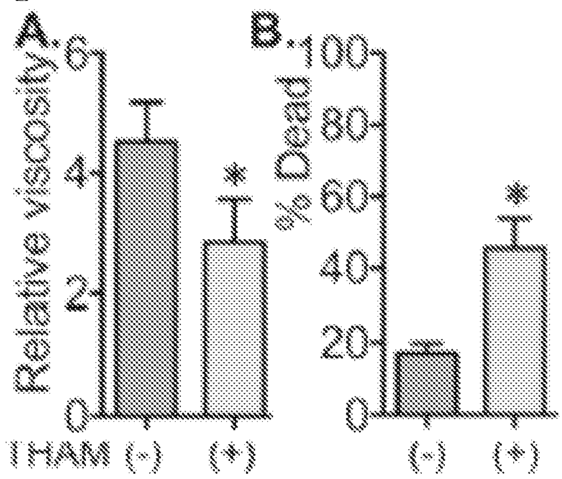
Figures 14A-14G
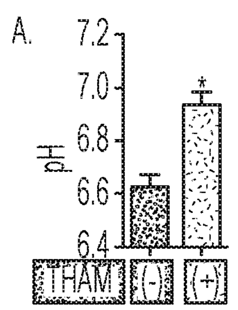
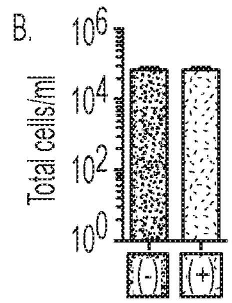
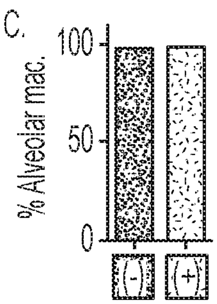
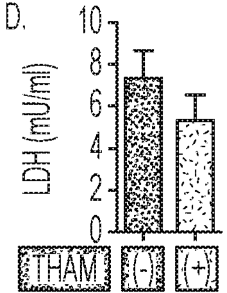
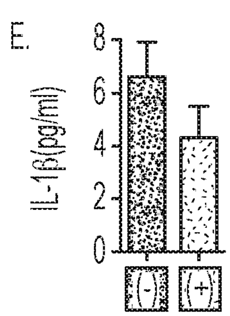
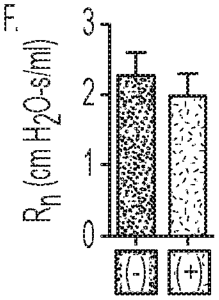
G.
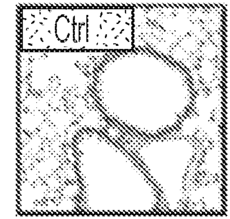
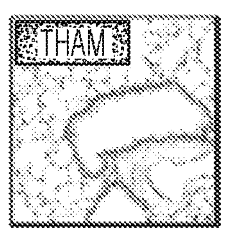

Figures 15A-15B
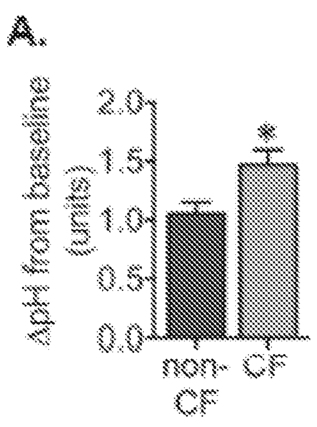
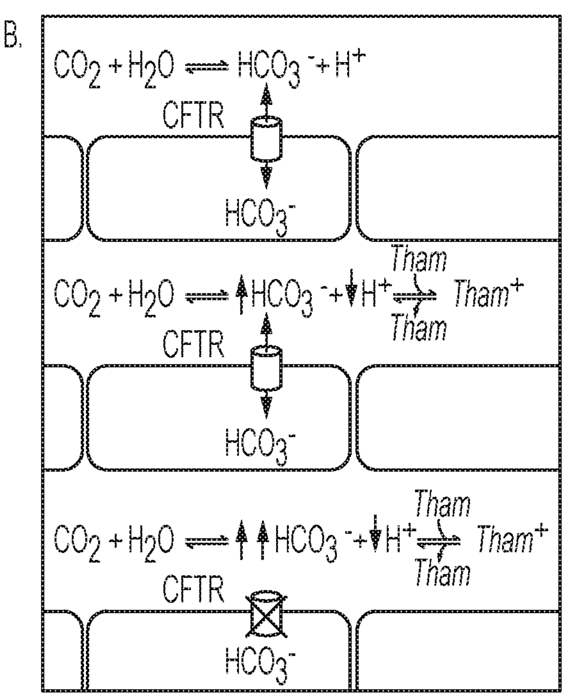
Figure 16
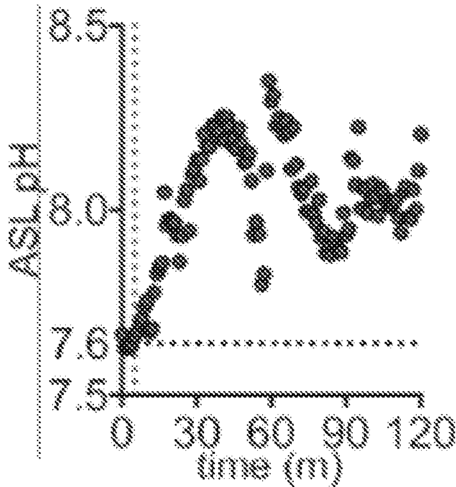

METHOD OF TREATING CYSTIC FIBROSIS AIRWAY DISEASE

PRIORITY APPLICATION

This application claims priority to U.S. Provisional Application No. 62/340,066 that was filed on May 23, 2016. The entire content of the application referenced above is hereby incorporated by reference herein.

STATEMENT REGARDING FEDERALLY SPONSORED RESEARCH

This invention was made with government support under grant HL091842 awarded by the National Institutes of Health. The government has certain rights in the invention.

BACKGROUND OF THE INVENTION

The pulmonary airway comprises those parts of the respiratory system through which air flows, conceptually beginning (on inhalation from the external environment) at the nose and mouth, and terminating in the alveoli. From the mouth or nose, inhaled air passes through the pharynx into the trachea, where it separates into the left and right main bronchi at the carina, situated at the level of the second thoracic vertebra. The main bronchi then branch into large bronchioles, one for each lobe of the lung. Within the lobes, the bronchioles further subdivide some twenty times, ending in clusters of alveoli.

The epithelial surfaces of the airway contain cilia. Inhaled particles adhere to mucus secreted by goblet cells, which is continuously driven outwards by the cilia. The epithelium of the airway also secretes a watery fluid upon which the mucus can ride freely. The production of this fluid is impaired by the disease cystic fibrosis. Macrophages in the airways help promote prophylaxis and prevent infection and contamination, by engulfing bacteria and other inhaled particles.

Disease conditions associated with the airway include cystic fibrosis, allergies, asthma, Chronic Obstructive Pulmonary Disease (COPD) and bronchitis. Cystic fibrosis (also known as CF or mucoviscidosis) is a common recessive genetic disease which affects the entire body, causing progressive disability and often early death. The name cystic fibrosis refers to the characteristic scarring (fibrosis) and cyst formation within the pancreas, first recognized in the 1930s. Difficulty breathing is the most serious symptom and results from frequent lung infections that are treated with, though not cured by, antibiotics and other medications. A multitude of other symptoms, including sinus infections, poor growth, diarrhea, and infertility result from the effects of CF on other parts of the body.

CF is caused by a mutation in the gene that encodes the cystic fibrosis transmembrane conductance regulator (CFTR) protein. This gene is required to regulate the components of sweat, digestive juices, and mucus. The CFTR protein, when positioned properly in the cell membrane, opens channels in the cell membrane. When the channels open, anions, including chloride and bicarbonate are released from the cells. Water follows by means of osmosis.

CF is most common among Caucasians; one in 25 people of European descent carry one allele for CF. Approximately 30,000 Americans have CF, making it one of the most common life-shortening inherited diseases in the United States. Individuals with cystic fibrosis can be diagnosed before birth by genetic testing or by a sweat test in early childhood. Ultimately, lung transplantation is often necessary as CF worsens.

Currently, there are no cures for cystic fibrosis, although there are several treatment methods. The management of cystic fibrosis has improved significantly over the years. While infants born with cystic fibrosis 70 years ago would have been unlikely to live beyond their first year, infants today are likely to live well into adulthood. The cornerstones of management are proactive treatment of airway infection and inflammation, and encouragement of good nutrition and an active lifestyle. Management of cystic fibrosis is aimed at maximizing organ function, and therefore quality of life. At best, current treatments delay the decline in organ function. Targets for therapy are the lungs, gastrointestinal tract (including pancreatic enzyme supplements), the reproductive organs (including assisted reproductive technology (ART)) and psychological support.

The most consistent aspect of therapy in cystic fibrosis is limiting and treating the lung damage caused by thick mucus and infection, with the goal of maintaining quality of life. Intravenous, inhaled, and oral antibiotics are used to treat chronic and acute infections. Mechanical devices and inhalation medications are used to alter and clear the thickened mucus. These therapies, while effective, can be extremely time-consuming for the patient. One of the most important battles that CF patients face is finding the time to comply with prescribed treatments while balancing a normal life.

Accordingly, a more effective, simple-to-administer, and efficient treatment for CF is needed.

SUMMARY OF THE INVENTION

In certain embodiments, the present invention provides a method of increasing liquid pH on a tissue surface in a mammalian need thereof comprising administering an effective amount of a therapeutic composition comprising tromethamine to the mammal. In certain embodiments, the method further comprises administering an effective amount of hypertonic saline. In certain embodiments, the mammal is a human.

In certain embodiments, the method further comprises administering an effective amount of $NaHCO_3$. In certain embodiments, $NaHCO_3$ is present at a concentration of about 1% to about 10%.

In certain embodiments, the method further comprises administering an antimicrobial agent. In certain embodiments, the antimicrobial agent is tobramycin, aztreonam, colistin, levofloxacin, ciprofloxacin, gentamicin, amikacin, or vancomycin.

In certain embodiments, the method further comprises administering mannitol, xylitol, pulmozyme, albuterol, atrovent, or mucomyst. In certain embodiments, the present invention provides a method of treating an airway infection in a patient in need thereof by administering an effective amount of a therapeutic composition comprising tromethamine to the patient. In certain embodiments, the method further comprises administering an effective amount of hypertonic saline.

In certain embodiments, the therapeutic composition is administered by aerosol inhalation, dry powder inhalation, liquid inhalation, liquid instillation, nasal lavage or sinus lavage. In certain embodiments, the present invention provides a method of treating a respiratory disease comprising administering an effective amount of a therapeutic composition comprising tromethamine and an effective amount of hypertonic saline to the patient. As used herein the term "treating" means having a therapeutic effect on the animal, such as preventing or ameliorating the symptoms of cystic fibrosis. As used herein the term "therapeutic effect" refers to a change in the associated abnormalities of the disease state, including pathological and behavioral deficits; a change in the time to progression of the disease state; a reduction, lessening, or alteration of a symptom of the disease; or an improvement in the quality of life of the person afflicted with the disease. Therapeutic effects can be measured quantitatively by a physician or qualitatively by a patient afflicted with the disease state targeted by the therapeutic agent. In certain embodiments, the respiratory disease is respiratory disease is cystic fibrosis (CF), non-cystic fibrosis bronchiectasis, chronic sinusitis, ventilator associated pneumonia, tracheostomy, lung transplant, COPD, asthma, or interstitial lung disease. In certain embodiments, the present invention provides a pharmaceutical formulation effective in treating respiratory disease consisting essentially of (a) an effective amount of tromethamine, (b) hypertonic saline, (c) a pharmaceutically acceptable carrier, (d) an antimicrobial agent, and (e) a standard CF pharmaceutical for the therapeutic treatment of the respiratory disease. In certain embodiments, the respiratory disease is cystic fibrosis (CF), non-cystic fibrosis bronchiectasis, chronic sinusitis, ventilator associated pneumonia, tracheostomy, lung transplant, COPD, asthma, or interstitial lung disease.

In certain embodiments, the present invention provides a pharmaceutical formulation effective in treating cystic fibrosis (CF), consisting essentially of (a) an effective amount of tromethamine, (b) hypertonic saline, (c) a pharmaceutically acceptable carrier, (d) an antimicrobial agent, and (e) a standard CF pharmaceutical to prepare a medicament for treatine cancer in an animal.

As used herein the term "consisting essentially of" is defined to mean that specified materials may optionally be included in the composition that do not materially affect the basic and novel characteristics of the claimed invention. Examples of such materials include preservatives and dispersants that do not have an impact on the pH-altering function of the therapeutic composition.

BRIEF DESCRIPTION OF DRAWINGS

FIGS. 5A-5C. Effect of tromethamine on tracheal airway surface liquid (ASL) pH of newborn piglets and ASL bacterial killing. A. Data are change in tracheal ASL pH of wild type newborn piglets after instillation of 250 μl 0.3M tromethamine. Data are mean±SEM, N=3, Wilcoxon signed-rank test. B. ASL pH in exposed tracheal window of CF piglets untreated (gray circles) and 15 min after tromethamine (closed circles). Data are mean±SEM; some error bars are hidden by symbols. N=6, Wilcoxon signed-rank test *<0.05. C. ASL bacterial killing in exposed tracheal window of CF piglets untreated (gray circles, N=4) and 15 min after tromethamine (closed circles, N=4-5). Data are mean±SEM, Wilcoxon-Mann-Whitney test, **<0.01.

FIGS. 6A-6D. Effect of tromethamine on nasal pH measurements. Data are nasal pH of healthy volunteers after instillation of 250 μl A. 0.3 M tromethamine (dashed line represent the duration of the effect of $HCO_3^-$) or B. 0.3 M xylitol (non-ionic control). Data are mean±SEM; some error bars are hidden by symbols, N=5, Wilcoxon signed-rank test, *<0.05. C. Nasal pH of subjects with cystic fibrosis (CF) at baseline and after instillation of 250 μl tromethamine. Bar graph on the left represents the mean pH±SEM. The graph on the right shows pH data from individual subjects over time. Data are mean±SEM; some error bars are hidden by symbols. N=6, One-way ANOVA with Holm-Sidak's Multiple Comparison Test, <0.01, *<0.005. D. Transepithelial voltage (Vt) in mV of CF subjects at baseline (gray circles) and 30 min (closed circles) after exposure to 250 μl 0.3 M tromethamine. N=6, Wilcoxon signed-rank test, not significant.

C. $HCO_3^-/CO_2$ and D. tromethamine. Results are from a single experiment. Each experiment was repeated at least 3 times with similar results.

FIG. 9. Demographics and lung function of the subjects that contributed sputum for the in vitro studies.

FIGS. 10A-10B. Loss of CFTR Causes an Acidic ASL pH. (A) Tracheal ASL pH in newborn non-CF (n=6) and CF (n=7) pigs. (B) Nasal ASL pH in non-CF (n=46) and CF (n=14) human neonates <3 mo. Data are mean±SEM. * p<0.05, t-test.

FIGS. 11A-11F. An Acidic ASL pH Causes Host Defense Defects. (A) Bacterial killing by tracheal ASL (grid assay). (B) Relationship between tracheal ASL pH and killing (grid assay) in pigs. p<0.01. (C) ASL relative viscosity (saline=1). (D) Relationship between pH and viscosity. ASL was collected from non-CF (dark) and CF (light) newborn pigs, incubated with 5 or 15% CO2 and viscosity determined. p<0.0001. (E) 3D airway reconstruction after IV methacholine at t=0 and 10 m of tracking period. Microdisk position is shown as spheres (enlarged 40×). Circle highlights particles that failed to clear. (F) MCT assay, % of time microdisks were stuck. Data are mean±SEM. n≥6 per genotype/panel. * p<0.05. Panels A, C, F t-test; B, D non-linear regression.

Figure 12:
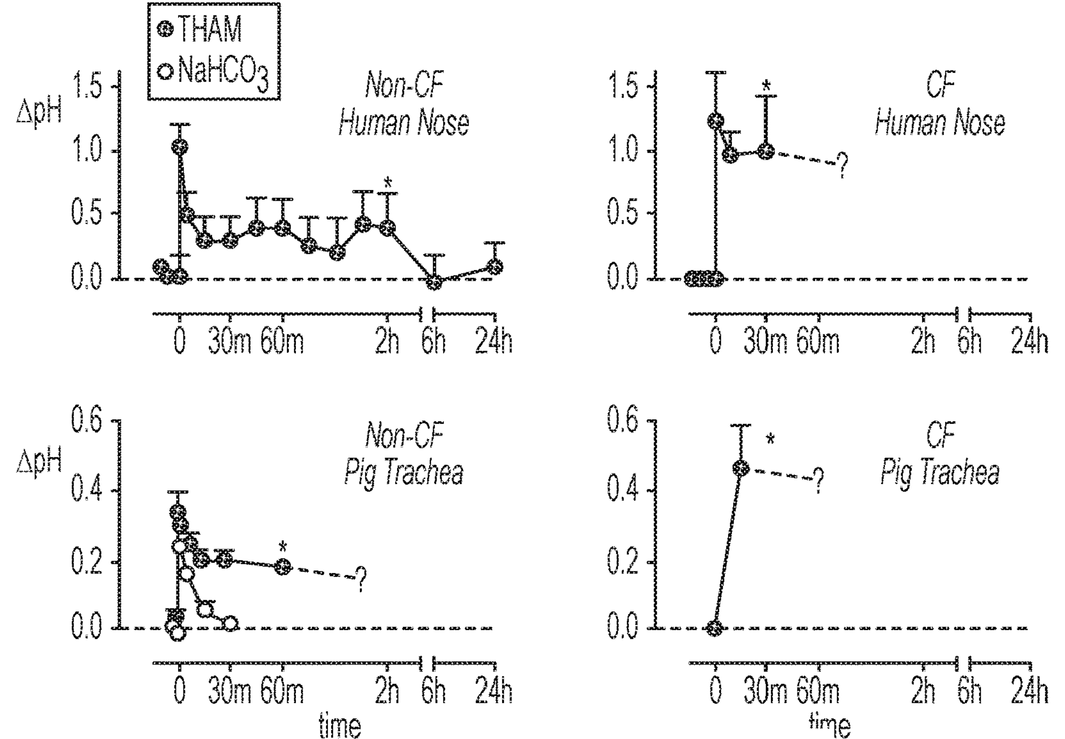

FIG. 12. THAM Alkalinizes Non-CF and CF ASL. THAM or $NaHCO_3$ was aerosolized into the nose (humans) or trachea (pigs) at t=0. Nasal or tracheal ASL pH was measured in healthy volunteers and CF subjects or non-CF/CF newborn pigs, respectively, after treatment. Shown are pH changes before and after treatment. Data are mean±SEM; some SEM bars are hidden by symbols, n=3-6/group, Wilcoxon signed-rank test, *p<0.05, compared to time=0.

FIGS. 13A-13B. THAM Alkalinization Decreases Mucus Viscosity and Enhances Bacterial Killing. (A) Effect of saline or THAM on ASL viscosity in humanCF airway cultures. (B) Effect of saline or THAM on human CF sputum bacterial killing with grid assay. Data are mean±SEM. n=6 individual donors/group. * p<0.05, t-test.

FIGS. 14A-14G. Aerosolized THAM is Safe. (A) BAL pH measured 3.5 hr after THAM inhalation. Mice were aerosolized with THAM (10× dose used in our prior human studies) or water (ctrl) in a whole-body exposure chamber for 3.5 hrs/d (5 d total). 3 d later mice were euthanized/studied. (B) BAL-total cell cts. (C) BAL-% alveolar macrophages. (D) BAL-LDH activity. (E) BAL-IL-1β (also no difference in other proinflammatory cytokines between groups, data not shown). (F) Airway resistance (FlexiVent). Baseline resistance did not differ between groups or following inhaled methacholine (MCh) dose-challenge (shown are 100 mg/ml MCh dose data). (G) Lung histology (HE). Data are mean±SEM. n=4-10/group. * p<0.05, t-test. Some SEM bars are hidden in mean bars.

FIGS. 15A-15B. THAM Alkalinizes CF Epithelia Greater than Non-CF. (A) THAM (1 μl) was applied to human n non-CF/CF airway epithelial cultures. pH was measured at 0 & 15 m with SNARF. Data are mean±SEM. n=6 donors/group. * p<0.05, t-test. (B) Model of THAM's prolonged effects in non-CF (top & middle) and CF (bottom) airways.

FIG. 16. Prolonged Airway Alkalinization by THAM. THAM was aerosolized into a sedated, non-CF newborn pig with a PARI LC-PLUS® nebulizer, using a cone mask over the snout. After sedation, a pH probe was passed through the vocal cords and into the distal mainstem bronchi. ASL pH was continuously measured. Verticle dotted line: completion of THAM nebulization. Horizontal dotted line: average pH prior to THAM.

Figure 17:
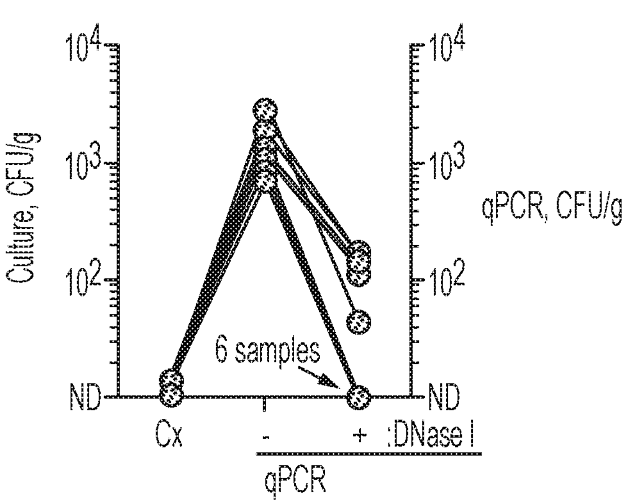

FIG. 17. DNase I Treatment Distinguishes Between "Live" vs "Dead" Bacteria. Bacteria were quantified in lung tissue by standard culture (Cx) and with 16S rRNA qPCR (CFU equivalents) using "universal" bacterial primers after DNase I or buffer control treatment before cell lysis. n=11 animals/group. Each set of data is from a different pig. ND=none detected.

Figures 18A, 18B:
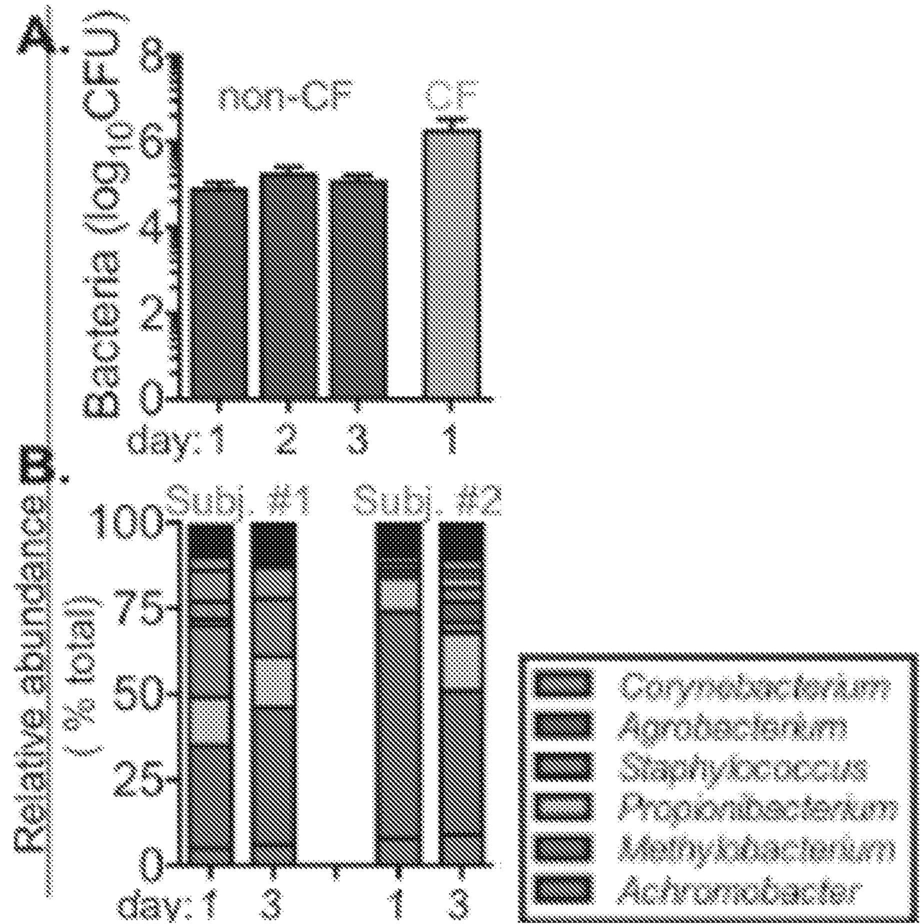

FIGS. 18A-18B. Human Nasal Bacterial Abundance and Composition are Stable. (A) Quantification of nasal bacteria in human non-CF and CF subjects. Both nares were swabbed and bacterial counts quantified using standard microbiology techniques. n=6 subjects/genotype. Bars are mean±SEM. (B) 16S rRNA sequencing was used to determine the relative abundance of bacterial taxa in nasal swab samples from 2 non-CF subjects on days 1 and 3. Colored segments represent the proportion of reads mapping to different taxa. Taxa present ≥5% are identified.

Figure 19:
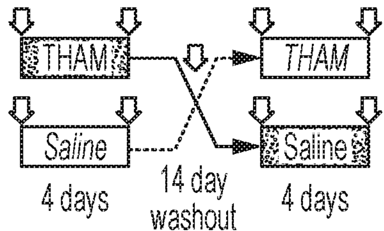

FIG. 19. Protocol for THAM Aerosolization in Humans. Arrows denote nasal sampling for bacteria and ASL collection.

Figure 20:
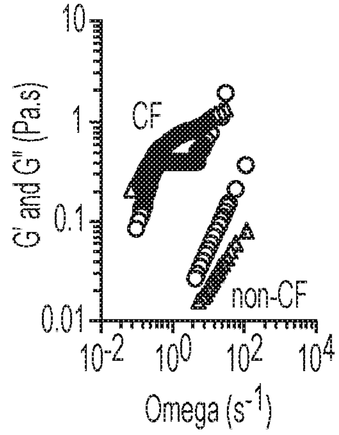

FIG. 20. CF Mucus has Greater Viscosity and Elasticity. Methacholine-stimulated ASL was collected from non-CF and CF newborn pigs. Fluorescent microspheres were mixed with mucus, imaged (2 min, 100 fps) with a high speed Nikon MR confocal, and using mean square displacement and the generalized Stokes-Einstein relation the viscoelastic properties (passive microrheology) were calculated. Triangles: storage/elastic modulus, G'. Circles: Loss/viscous modulus, G".

Figures 21A, 21B, 21C:
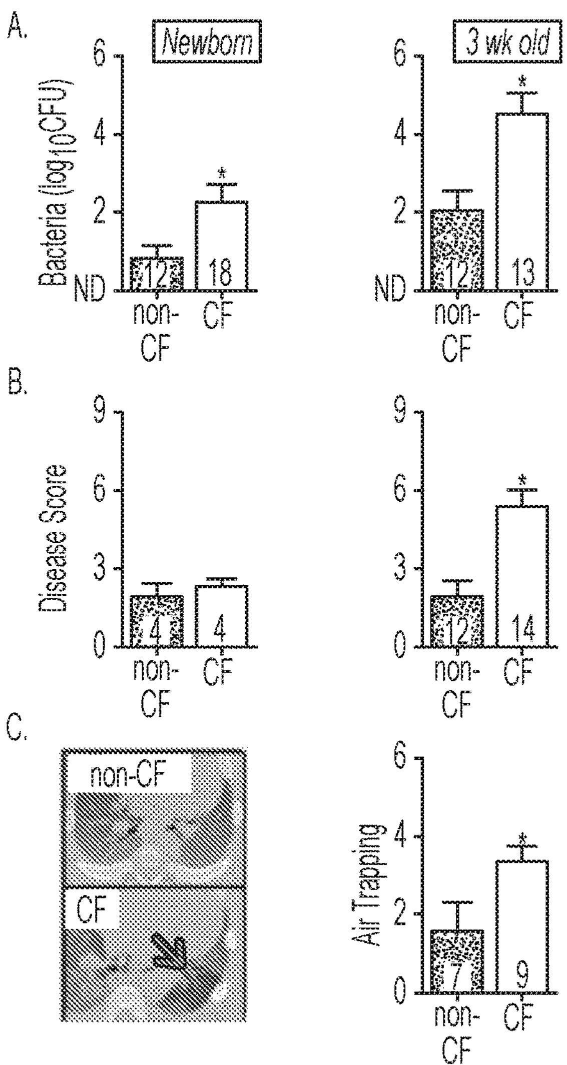
Figures 22A, 22B, 22C, 22D:
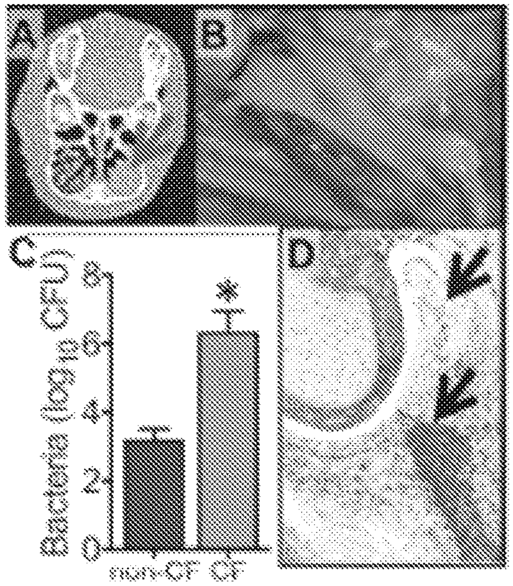

FIGS. 21A-21C. CF Pigs Develop Lung Disease Within 3 Wks. (A) Lung bacteria (CFU/g tissue). (B) Histology disease score. For details, see section 3a.iv. (C) CT assessment of air trapping (AT). L panel: CT slice from non-CF & CF pig (~3 wks old, arrow=AT). R panel: AT quantification. 0=no AT; 6=AT in all 6 lung zones (right/leftupper, middle, lower). Shown are mean±SEM. # of individual animals/group are shown in bars. *p<0.05, t-test.

FIGS. 22A-22D. CF Pigs Develop Sinus Disease. (A) CT (red arrow: sinus obstruction), (B) Necropsy (mucopurulent material), (C) Microbiology (total bacteria/sample, n=8/group), and (D) Histology (black arrows: mucopurulent material) of sinuses from 3 wk old CF pigs. Data are mean±SEM. * p<0.05, t-test.

DETAILED DESCRIPTION OF THE INVENTION

In cystic fibrosis (CF), loss of cystic fibrosis transmembrane conductance regulator (CFTR) anion channel activity causes airway surface liquid (ASL) pH to become acidic, which impairs airway host defenses. One potential therapeutic approach is to correct the acidic pH in CF airways by aerosolizing $HCO_3^-$ and/or non-bicarbonate pH buffers. Here, it is shown that raising ASL pH with inhaled $HCO_3^-$ increased pH. However, the effect was transient, and pH returned to baseline values within 30 minutes. Tromethamine (or Tham) is a buffer with a long serum half-life used as an intravenous formulation to treat metabolic acidosis. It was found that tromethamine aerosols increased ASL pH in vivo for at least 2 hours and enhanced bacterial killing. Inhaled hypertonic saline (7% NaCl) is delivered to people with CF in an attempt to promote mucus clearance. Because an increased ionic strength inhibits ASL antimicrobial factors, tromethamine was added to hypertonic saline and applied it to CF sputum. It was found that tromethamine alone and in combination with hypertonic saline increased pH and enhanced bacterial killing. Thus, aerosolizing the $HCO_3^-$-independent buffer tromethamine, either alone or in combination with hypertonic saline, provides therapeutic benefit in CF airway disease.

In certain embodiments, the present invention provides a method of increasing liquid pH on airway surface of a tissue in a patient in need thereof comprising administering an effective amount of a therapeutic composition comprising tromethamine to the patient. In certain embodiments, the therapeutic composition consists essentially of tromethamine. In certain embodiments, the tromethamine is at a concentration of about 0.36 g/l to about 200 g/l. In certain embodiments, the tissue is contacted on its mucosal surface.

In certain embodiments, the method further comprises administering an effective amount of hypertonic saline. In certain embodiments, the hypertonic saline comprises NaCl at a concentration of 1% to 8%. In certain embodiments, the NaCl is at a concentration of about 7%.

In certain embodiments, the therapeutic composition and the hypertonic saline are administered simultaneously or sequentially.

In certain embodiments, the method further comprises administering an effective amount of $NaHCO_3$. In certain embodiments, $NaHCO_3$ is present at a concentration of about 1% to about 10%.

In certain embodiments, the therapeutic composition is administered orally, by aerosol inhalation (e.g., intra-airway, such as tracheal or bronchial inhalation), dry powder inhalation, liquid inhalation, liquid instillation, bronchoscopic instillation, nasal lavage or sinus lavage. In certain embodiments, the subject is a mammal, such as a human. In certain embodiments the symptoms are reduced by at least 1%, 5%, 10%, 20, 30%, 40%, 50%, 60%, 70%, 80%, 90% 95%, or 99%.

In certain embodiments, the present invention provides a method of treating an airway infection in a patient in need thereof by administering an effective amount of a therapeutic composition comprising tromethamine to the patient. In certain embodiments, the therapeutic composition consists essentially of tromethamine. In certain embodiments, the tromethamine is at a concentration of about 0.36 g/l to about 200 g/l.

In certain embodiments, the method further comprises administering an effective amount of hypertonic saline. In certain embodiments, the hypertonic saline comprises NaCl at a concentration of about 1% to about 8%. In certain embodiments, the NaCl is at a concentration of about 7%.

In certain embodiments, the therapeutic composition and the hypertonic saline are administered simultaneously or sequentially.

In certain embodiments, the method further comprises administering an effective amount of $NaHCO_3$. In certain embodiments, $NaHCO_3$ is present at a concentration of about 1% to about 10%.

In certain embodiments, the therapeutic composition is administered by orally, by aerosol inhalation (e.g., intra-airway, such as tracheal or bronchial inhalation), dry powder inhalation, liquid inhalation, liquid instillation, bronchoscopic instillation, nasal lavage or sinus lavage. In certain embodiments, the method further comprises administering an antimicrobial agent. In certain embodiments, the antimicrobial agent is tobramycin, aztreonam, colistin, levofloxacin, ciprofloxacin, gentamicin, amikacin, vancomycin, hBD-3 and/or LL-37. In certain embodiments, the antimicrobial agent is hBD-3 and/or LL-37.

In certain embodiments, the liquid pH on the airway surface is increased by one pH unit.

In certain embodiments, the liquid pH on the airway surface is increased for more than one hour.

In certain embodiments, the method further comprises administering mannitol, xylitol, pulmozyme, albuterol, atrovent, and/or mucomyst.

In certain embodiments, the present invention provides a method of treating a respiratory disease in a patient comprising administering an effective amount of a therapeutic composition comprising tromethamine and an effective amount of hypertonic saline to the patient. In certain embodiments, the respiratory disease is cystic fibrosis (CF), non-cystic fibrosis bronchiectasis, chronic sinusitis, ventilator associated pneumonia, tracheostomy, lung transplant, COPD, asthma, or interstitial lung disease. In certain embodiments, the respiratory disease is CF.

In certain embodiments, the present invention provides a pharmaceutical formulation effective in treating cystic fibrosis (CF), consisting essentially of (a) an effective amount of tromethamine, (b) hypertonic saline, (c) a pharmaceutically acceptable carrier, (d) an antimicrobial agent, and (e) a standard CF pharmaceutical for the therapeutic treatment of CF.

In certain embodiments, the pharmaceutical formulation consists of (a) an effective amount of tromethamine, (b) hypertonic saline, and (c) a pharmaceutically acceptable carrier.

In certain embodiments, the present invention provides a pharmaceutical formulation effective in treating cystic fibrosis (CF), consisting essentially of (a) an effective amount of tromethamine, (b) hypertonic saline, (c) a pharmaceutically acceptable carrier, (d) an antimicrobial agent, and (e) a standard CF pharmaceutical to prepare a medicament for treatine cancer in an animal. In certain embodiments, the animal is a mammal, such as a human.

In certain embodiments, the pharmaceutical formulation consists of (a) an effective amount of tromethamine, (b) hypertonic saline, and (c) a pharmaceutically acceptable carrier.

In certain embodiments, the facilitating agent and/or therapeutic agent is administered orally, by inhalation, by aerosol, dry powder, bronchoscopic instillation, or intra-airway (tracheal or bronchial) aerosol. In certain embodiments, the therapeutic RNAi agent is present within a pharmaceutical composition. In certain embodiments, the airway epithelial disease is cystic fibrosis. In certain embodiments, the subject is a mammal, such as a human. In certain embodiments the symptoms are reduced by at least 1%, 5%, 10%, 20, 30%, 40%, 50%, 60%, 70%, 80%, 90% 95%, or 99%.

Administration of Therapeutic Agent

The therapeutic agent is administered to the patient so that the therapeutic agent contacts cells of the patient's respiratory. For example, the therapeutic agent may be administered directly via an airway to cells of the patient's respiratory system. The therapeutic agent can be administered intranasally (e.g., nose drops) or by inhalation via the respiratory system, such as by propellant based metered dose inhalers or dry powders inhalation devices.

Formulations suitable for administration include liquid solutions. Liquid formulations may include diluents, such as water and alcohols, for example, ethanol, benzyl alcohol, propylene glycol, glycerin, and the polyethylene alcohols, either with or without the addition of a pharmaceutically acceptable surfactant, suspending agent, or emulsifying agent. The therapeutic agent can be administered in a physiologically acceptable diluent in a pharmaceutically acceptable carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

The therapeutic composition or agent, alone or in combination with other suitable components, can be made into aerosol formulations to be administered via inhalation. These aerosol formulations can be placed into pressurized acceptable propellants, such as dichlorodifluoromethane, propane, and nitrogen. Such aerosol formulations may be administered by metered dose inhalers. They also may be formulated as pharmaceuticals for non-pressured preparations, such as in a nebulizer or an atomizer. In certain embodiments, administration may be, e.g., aerosol, instillation, intratracheal, intrabronchial or bronchoscopic deposition.

In certain embodiments, the therapeutic agent may be administered in a pharmaceutical composition. Such pharmaceutical compositions may also comprise a pharmaceutically acceptable carrier and other ingredients known in the art. The pharmaceutically acceptable carriers described herein, including, but not limited to, vehicles, adjuvants, excipients, or diluents, are well-known to those who are skilled in the art. Typically, the pharmaceutically acceptable carrier is chemically inert to the active compounds and has no detrimental side effects or toxicity under the conditions of use. The pharmaceutically acceptable carriers can include polymers and polymer matrices. Viscoelastic gel formulations with, e.g., methylcellulose and/or carboxymethylcellulose may be beneficial (see Sinn et al., *Am J Respir Cell Mol Biol,* 32(5), 404-410 (2005)).

The therapeutic agent can be administered by any conventional method available for use in conjunction with pharmaceuticals, either as individual therapeutic agents or in combination with at least one additional therapeutic agent.

In certain embodiments, the therapeutic agent are administered with an agent that disrupts, e.g., transiently disrupts, tight junctions, such as EGTA (see U.S. Pat. No. 6,855,549).

The total amount of the therapeutic agent administered will also be determined by the route, timing and frequency of administration as well as the existence, nature, and extent of any adverse side effects that might accompany the administration of the compound and the desired physiological effect. It will be appreciated by one skilled in the art that various conditions or disease states, in particular chronic conditions or disease states, may require prolonged treatment involving multiple administrations.

The therapeutic agent can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The therapeutic agent may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be sprayed onto the affected area using pump-type or aerosol sprayers.

Useful dosages of the therapeutic agent can be determined by comparing their in vitro activity, and in vivo activity in animal models. Methods for the extrapolation of effective dosages in mice, and other animals, to humans are known to the art; for example, see U.S. Pat. No. 4,938,949.

The amount of the therapeutic agent, or an active salt or derivative thereof, required for use in treatment will vary not only with the particular salt selected but also with the route of administration, the nature of the condition being treated and the age and condition of the patient and will be ultimately at the discretion of the attendant physician or clinician.

Pharmaceutical compositions are administered in an amount, and with a frequency, that is effective to inhibit or alleviate the symptoms of cystic fibrosis and/or to delay the progression of the disease. The effect of a treatment may be clinically determined by nasal potential difference measurements as described herein. The precise dosage and duration of treatment may be determined empirically using known testing protocols or by testing the compositions in model systems known in the art and extrapolating therefrom. Dosages may also vary with the severity of the disease. A pharmaceutical composition is generally formulated and administered to exert a therapeutically useful effect while minimizing undesirable side effects. In general, an oral dose ranges from about 200 mg to about 1000 mg, which may be administered 1 to 3 times per day. Compositions administered as an aerosol are generally designed to provide a final concentration of about 10 to 50 μM at the airway surface, and may be administered 1 to 3 times per day. It will be apparent that, for any particular subject, specific dosage regimens may be adjusted over time according to the individual need. In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Compounds of the invention can also be administered in combination with other therapeutic agents, for example, other agents that are useful to treat cystic fibrosis. Examples of such agents include antibiotics. Accordingly, in one embodiment the invention also provides a composition comprising a therapeutic agent, or a pharmaceutically acceptable salt thereof, at least one other therapeutic agent, and a pharmaceutically acceptable diluent or carrier. The invention also provides a kit comprising a therapeutic agent, or a pharmaceutically acceptable salt thereof, at least one other therapeutic agent, packaging material, and instructions for administering the therapeutic agent or the pharmaceutically acceptable salt thereof and the other therapeutic agent or agents to an animal to treat cystic fibrosis.

A pharmaceutical composition may be prepared with carriers that protect active ingredients against rapid elimination from the body, such as time release formulations or coatings. Such carriers include controlled release formulations, such as, but not limited to, microencapsulated delivery systems, and biodegradable, biocompatible polymers, such as ethylene vinyl acetate, polyanhydrides, polyglycolic acid, polyorthoesters, polylactic acid and others known to those of ordinary skill in the art.

In certain embodiments, the therapeutic agent is directly administered as a pressurized aerosol or nebulized formulation to the patient's lungs via inhalation. Such formulations may contain any of a variety of known aerosol propellants useful for endopulmonary and/or intranasal inhalation administration. In addition, water may be present, with or without any of a variety of cosolvents, surfactants, stabilizers (e.g., antioxidants, chelating agents, inert gases and buffers). For compositions to be administered from multiple dose containers, antimicrobial agents are typically added. Such compositions are also generally filtered and sterilized, and may be lyophilized to provide enhanced stability and to improve solubility.

As noted above, a therapeutic agent may be administered to a mammal to stimulate chloride transport, and to treat cystic fibrosis. Patients that may benefit from administration of a therapeutic compound as described herein are those afflicted with cystic fibrosis. Such patients may be identified based on standard criteria that are well known in the art, including the presence of abnormally high salt concentrations in the sweat test, the presence of high nasal potentials, or the presence of a cystic fibrosis-associated mutation. Activation of chloride transport may also be beneficial in other diseases that show abnormally high mucus accumulation in the airways, such as asthma and chronic bronchitis. Similarly, intestinal constipation may benefit from activation of chloride transport by the therapeutic agents provided herein.

The term "therapeutically effective amount," in reference to treating a disease state/condition, refers to an amount of a compound either alone or as contained in a pharmaceutical composition that is capable of having any detectable, positive effect on any symptom, aspect, or characteristics of a disease state/condition when administered as a single dose or in multiple doses. Such effect need not be absolute to be beneficial.

The terms "treat," "treating" and "treatment" as used herein include administering a compound prior to the onset of clinical symptoms of a disease state/condition so as to prevent any symptom, as well as administering a compound after the onset of clinical symptoms of a disease state/condition so as to reduce or eliminate any symptom, aspect or characteristic of the disease state/condition. Such treating need not be absolute to be useful.

Example 1

Use of Tromethamine as Inhaled Therapy to Treat CF Airway Disease

Introduction

Airways evolved with a thin layer of fluid, the airway surface liquid (ASL), that is rich in host defense mechanisms and strategically situated at the interface with the environment. Appropriate ASL volume, pH and ionic composition are critical for optimal airway host defense. In cystic fibrosis (CF), dysfunction of an anion channel, cystic fibrosis transmembrane conductance regulator (CFTR), inhibits two important airway host defenses: antimicrobial factors and mucociliary transport. Loss of CFTR mediated $HCO_3^-$ secretion acidifies ASL pH and inhibits antimicrobial factors. Loss of $Cl^-$ and $HCO_3^-$ secretion also alters the viscoelastic properties of mucus and reduces mucociliary transport. With these and potentially other host defense impairments, the airways fail to eradicate and dispose of invading microorganisms. As a result, recurrent airway infections and inflammation cause a progressive decline in lung function. Despite advances in antibiotic therapy and mucus clearing maneuvers, airway disease continues to shorten the lives of people with CF.

In newborn CF piglets, acidic ASL pH inhibits antimicrobial factors. Instillation of $HCO_3^-$ onto the airway surface of CF piglet trachea raised ASL pH and enhanced bacterial killing. Conversely, acidifying the ASL of non-CF piglets by increasing $CO_2$ tension inhibited bacterial killing. Small changes in ASL pH resulted in a large defect in bacterial killing due to the inhibitory effect of acidic pH on both individual antimicrobial factors and on their synergistic interactions.

Another important arm of the airway host defense is mucociliary transport. Mucociliary transport was impaired in vivo in CF piglets. In freshly excised trachea, impaired mucus detachment from CF submucosal glands disrupted mucociliary transport, although it remains uncertain whether defective $HCO_3^-$ secretion, liquid secretion, or a combination are responsible. Additional studies revealed that an acidic pH increased ASL viscosity.

One potential therapeutic approach to raise ASL pH is to aerosolize pH buffers. Indeed, a clinical trial of aerosolized $HCO_3^-$ in humans with CF is ongoing (ClinicalTrials.gov). Tromethamine (THAM® or tris(hydroxymethyl)aminomethane acetate) is an FDA approved buffer, in clinical use to reverse metabolic acidosis (Luchsinger P C. The use of 2-amino-2-hydroxymethyl-1,3-propanediol in the management of respiratory acidosis. Ann N Y Acad Sci. 1961; 92:743-50. PubMed PMID: 13764013; Nahas G G, Sutin K M, Fermon C, Streat S, Wiklund L, Wahlander S, et al. Guidelines for the treatment of acidaemia with THAM. Drugs. 1998; 55(2):191-224. PubMed PMID: 9506241; Brasch H, Thies E, Iven H. Pharmacokinetics of TRIS (hydroxymethyl-)aminomethane in healthy subjects and in patients with metabolic acidosis. Eur J Clin Pharmacol. 1982; 22(3):257-64. PubMed PMID: 7106159). In contrast to the short-term effect of intravenous $NaHCO_3$, tromethamine alkalinizes serum with an effect that persists for 16-48 hours. Tromethamine is also used as an excipient for inhaled preparations of prostacyclin (Actelion Pharmaceuticals US I. Ventavis® (iloprost) inhalation solution. Prescribing information. 2009) and nasal preparations of ketorolac (Quadir M, Zia H, Needham T E. Development and evaluation of nasal formulations of ketorolac. Drug Deliv. 2000; 7(4):223-9. doi: 10.1080/107175400455155. PubMed PMID: 11195429). Because tromethamine has a long half-life and prolonged buffering capacity in serum, it was hypothesized that inhaled tromethamine would increase ASL pH for a longer duration than $HCO_3^-$ and would enhance ASL bacterial killing. This hypothesis was tested in both pigs and humans with CF.

Figures 1A, 1B:
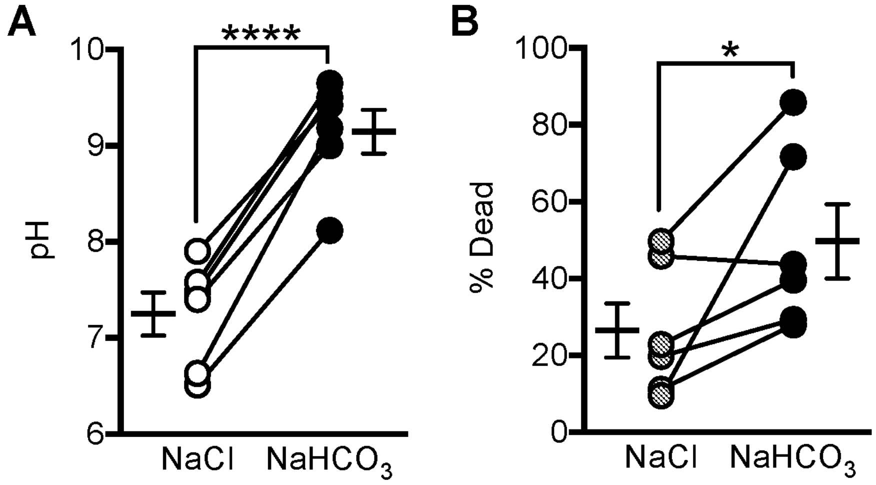
FIGS. 1A-1B. Cystic fibrosis (CF) sputum antimicrobial activity in the presence of $NaHCO_3$. A. CF sputum pH. B. CF sputum antimicrobial activity, in the presence of 200 mM NaCl or 200 mM $NaHCO_3$ (1:1 v/v) at 5% $CO_2$. Data are mean±SEM; some error bars are hidden by symbols. Each data point indicates sputum from a different donor N=6. *<0.05, ****<0.001 from a Wilcoxon signed-rank test.

Results $NaHCO_3$ Increases the pH of CF Sputum and Enhances its Antibacterial Activity To investigate the effect of increasing CF sputum pH on bacterial killing, sputa was collected from individuals with CF. Each sputum sample was mixed with an equal volume of either $NaHCO_3$ or NaCl. pH was measured in a humidified chamber at fixed 5% $CO_2$ using a planar opto-electrode. Bacterial killing was also measured. Compared to an equimolar concentration of NaCl, $NaHCO_3$ increased sputum pH (FIG. 1A). The bacterial killing properties of CF sputum by was interrogated by examining the viability of *S. aureus*, one of the first bacteria to infect CF lungs. *S. aureus* was attached to small gold grids and the antibacterial properties of the sputum-buffer mixture was probed (Pezzulo A A, Tang X X, Hoegger M J, Alaiwa M R, Ramachandran S, Moninger T O, et al. Reduced airway surface pH impairs bacterial killing in the porcine cystic fibrosis lung. Nature. 2012; 487(7405): 109-13. Epub 2012/07/06. doi: 10.1038/nature11130. PubMed PMID: 22763554; PubMed Central PMCID: PMC3390761). The grids were recovered 15 minutes later and *S. aureus* viability was examined. $NaHCO_3$ increased the CF sputum ability to kill *S. aureus* in comparison to an equimolar concentration of NaCl (FIG. 1B). These data indicate that adding $NaHCO_3$ raises CF sputum pH and enhances its ability to rapidly kill bacteria.

$NaHCO_3$ Transiently Increases Nasal pH

Figures 2A, 2B, 2C, 2D, 2E, 2F, 2G:
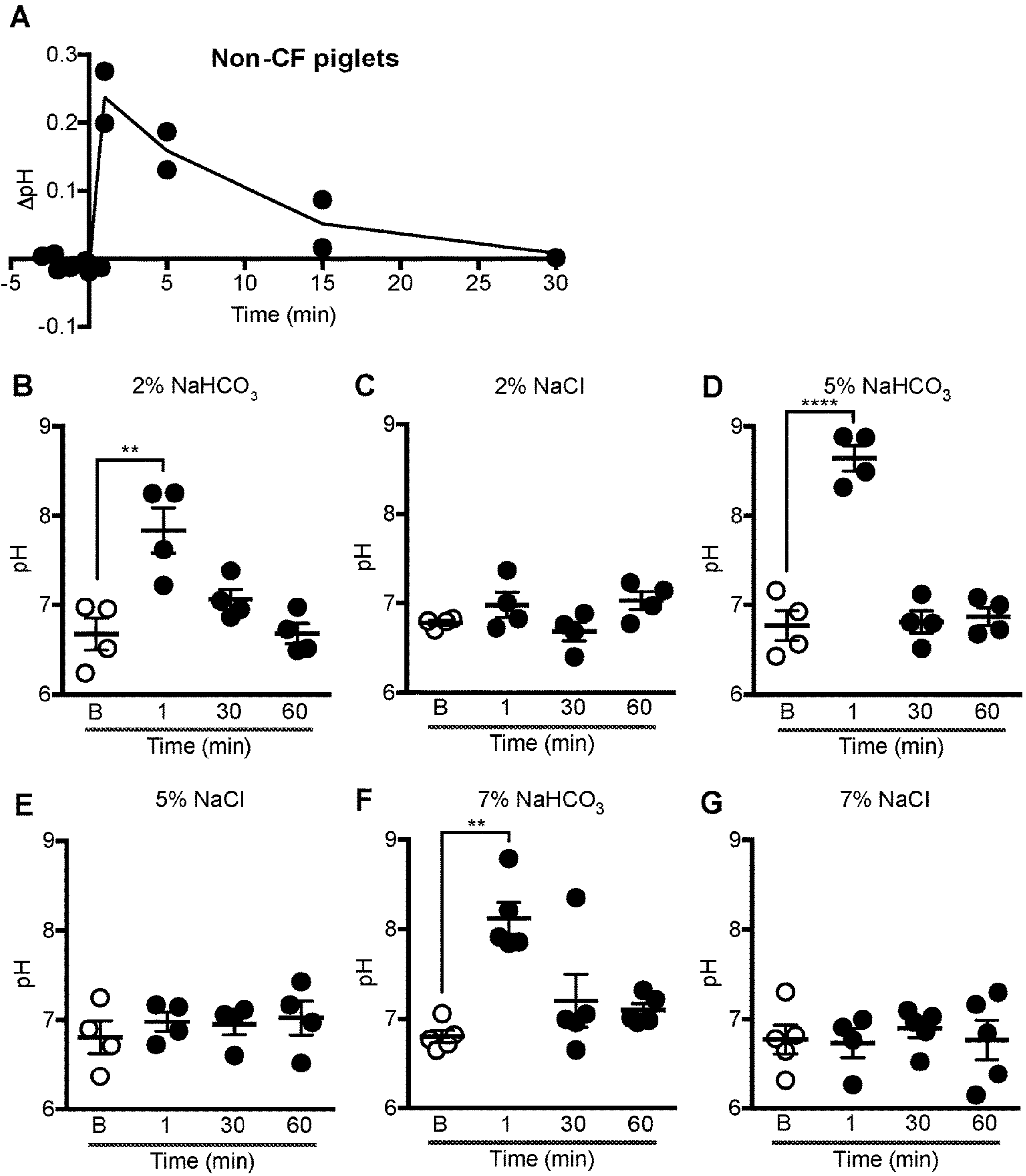
FIGS. 2A-2G. Effect of $NaHCO_3$ on airway surface liquid (ASL) pH. A. Data are change in tracheal ASL pH of wild type newborn piglets after instillation of 250 μl 200 mM $NaHCO_3$. Each data point indicates measurements from a different animal, N=2. (B to G) Data are human nasal pH at baseline and after instillation of 250 μl B. 2% $NaHCO_3$. C. 2% NaCl. D. 5% $NaHCO_3$. E. 5% NaCl. F. 7% $NaHCO_3$. G. 7% NaCl. Data are mean±SEM; some error bars are hidden by symbols. N=4-5, One-way ANOVA. <0.01, **<0.001.

Nebulized $NaHCO_3$ is used safely in patients suffering from acute chlorine gas inhalational injury. In that clinical setting, the goal is an immediate neutralizing effect from $NaHCO_3$. However, in CF airways a longer effect may be required. To test the effect of $NaHCO_3$, 250 μl of 200 mM $NaHCO_3$ was aerosolized onto the surgically exposed trachea of non-CF piglets and ASL pH was measured. $NaHCO_3$ alkalinized ASL pH, but the effect was short-lived and returned to baseline within 30 minutes (FIG. 2A). In addition, 250 μl of 2% (238 mM) $NaHCO_3$ was aerosolized into the nose of healthy human volunteer subjects. Similar to the findings on the porcine tracheal surface, $NaHCO_3$ increased ASL pH, but pH returned to baseline within 60 minutes (FIG. 2B, 2C). Increasing the concentration of $NaHCO_3$ to 5% or 7% had no additional effect on the duration of the rise in nasal pH (FIG. 2D, 2E, 2F, 2G). Thus, these data suggest that the effect of $NaHCO_3$ on ASL pH is transient. Possible explanations include transepithelial $HCO_3^-$ absorption and/or a rapid shift of $HCO_3^-$ to $CO_2$ and $H_2O$.

Figure 3A:
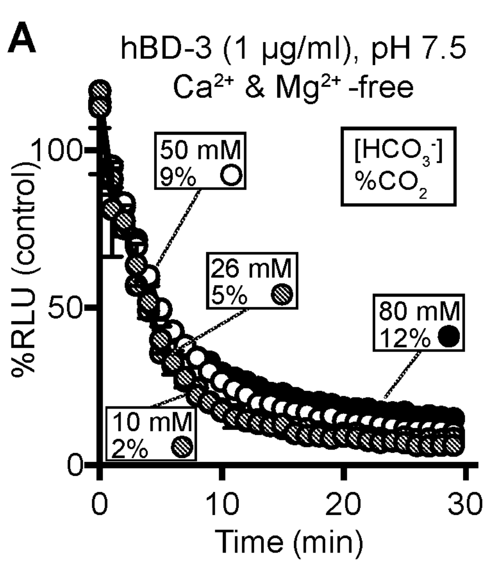
FIGS. 3A-3D. Antimicrobial activity of cathelicidin (LL-37) or human beta-Defensin-3 (hBD-3) in the presence of varying concentrations of $NaHCO_3$. Data are relative luminescence (RLU) of *S. aureus* (Xen-29) as a percentage of control (no added antimicrobial and same buffer conditions) at isohydric pH (same pH of 7.5) and varying concentration of $NaHCO_3$/% $CO_2$ (light gray circles, $NaHCO_3$10 mM/$CO_2$ 2%; dark gray circles, $NaHCO_3$26 mM/$CO_2$ 5%, open circles $NaHCO_3$50 mM/$CO_2$ 9%, closed circles $NaHCO_3$ 80 mM/$CO_2$ 12%) in the presence. (A and B) in the absence of $Ca^{2+}$& $Mg^{2+}$. A. 1 μg/ml hBD-3. B. 100 μm/ml LL-37. (C and D) in the presence of 1 mM $Ca^{2+}$& 1 mM $Mg^{2+}$. C. 5 μg/ml hBD-3. D. 100 μm/ml LL-37. Data are mean±SEM; some error bars are hidden by symbols. Results are from a single experiment in triplicate. Each experiment was repeated at least 3 times with similar results.
Figure 3B:
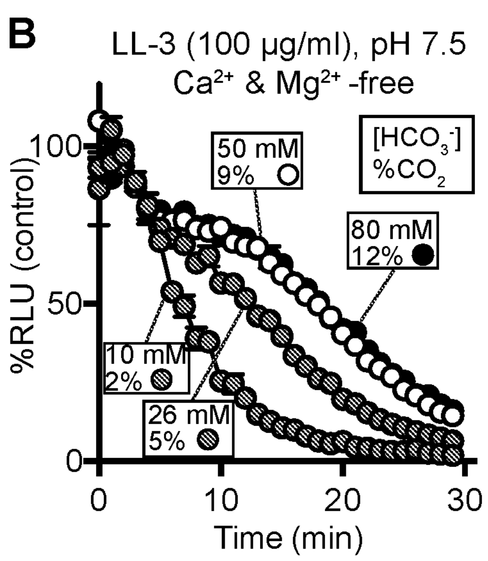
Figure 3C:
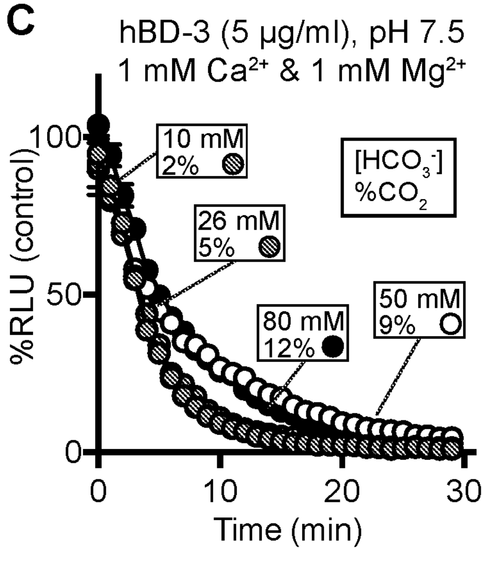
Figure 3D:
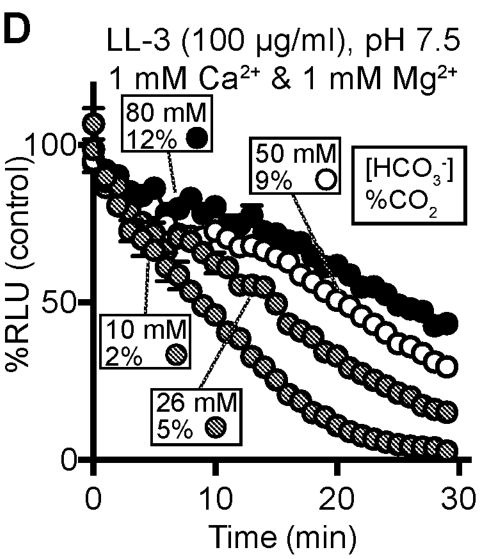

$HCO_3^-$ is not Required for a pH-Related Increase in ASL Antimicrobial Activity The transient effect of $HCO_3^-$ on ASL pH prompted the inventors to find buffers with a longer duration. ASL antimicrobial activity is pH regulated, yet it remains uncertain whether $HCO_3^-$ regulates antimicrobial activity independently of its effect on pH. If $HCO_3^-$ is not required, then any buffer that increases ASL pH may have a therapeutic potential in CF airways. To investigate whether or not, at a constant pH, $HCO_3^-$ enhances cationic peptide activity, the antimicrobial properties of hBD-3 (an antimicrobial peptide that is inhibited by ionic strength and $Ca^{2+}$) were tested and LL-37 (not inhibited by ionic strength or $Ca^{2+}$) at different concentrations of $HCO_3^-$ and a constant pH of 7.5. It was found that increasing $HCO_3^-$ concentration, in the absence of $Ca^{2+}$ did not increase hBD-3 and LL-37 activity, and in fact it slightly inhibited their activity (FIG. 3A, 3B). In the presence of $Ca^{2+}$, it was found that increasing $HCO_3^-$ inhibited both hBD-3 and LL-37 antimicrobial activity (FIG. 3C, 3D). These data suggest that under a constant alkaline pH, increasing $HCO_3^-$ concentrations does not enhance hBD-3 and LL-37 antimicrobial activity; on the contrary it inhibits to a small degree. These data, together with the prior finding that increasing pH enhances ASL antimicrobials, suggest that any buffer that can increase pH might be used therapeutically to alkalinize ASL in CF.

Tromethamine Buffers in the ASL Physiological pH Range

One possible candidate is tromethamine (tris(hydroxymethyl)aminomethane), an amine compound with pKa of 8.07 at 25° C. Tromethamine has a long half-life when given intravenously and controls pH in the physiological range (Nahas G G, Sutin K M, Fermon C, Streat S, Wiklund L, Wahlander S, et al. Guidelines for the treatment of acidaemia with THAM. Drugs. 1998; 55(2):191-224. PubMed PMID: 9506241). The buffering capacity of 0.3 M tromethamine and 0.3 M $NaHCO_3$ (equilibrated with 5% $CO_2$) were measured. Both buffers were titrated with 0.1 M HCl and calculated the buffering capacity (β), the acid equivalents needed to change the pH of a buffer by 1 pH unit. By plotting the acid titration curve of both $NaHCO_3$ and tromethamine (Supp. 1A, 1B) and the first derivative (Supp. 1C, 1D) against pH, it was found that $NaHCO_3$ had a significant buffering capacity at a pH range from 6 to 7 (Supp. 1C), whereas tromethamine had a buffering capacity at a slightly broader pH range from 6.5 to 8.5 (Supp. 1D). Moreover, tromethamine had an additional buffering range at lower pH values (pH 3-6). These data suggest that tromethamine has an optimal buffering capacity that is within the pH range of both CF and non-CF ASL and a wider range than $HCO_3^-/CO_2$.

Tromethamine Enhances hBD-3 and LL-37 Antimicrobial Activity

Figures 4A, 4B:
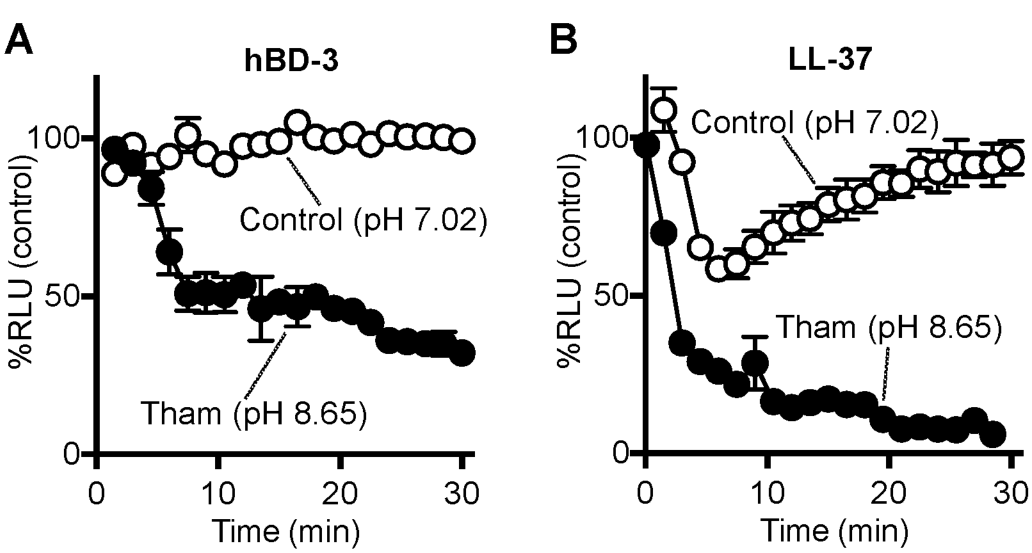
FIGS. 4A-4B. Effect of tromethamine on cathelicidin (LL-37) or human beta-Defensin-3 (hBD-3) antimicrobial activity. Data are relative luminescence (RLU) of *S. aureus* (Xen-29) as a percentage of control (no added antimicrobial and same buffer conditions) at an ionic strength of 125 mM (1% Tryptic soy broth, 100 mM NaCl) in the presence of 10 mM xylitol (non-ionic control, open circles, pH 7.02) or 10 mM tromethamine (closed circles, pH 8.65) and A. 1 μg/ml hBD-3. B. 10 μg/ml LL-37. Data are mean±SEM; some error bars are hidden by symbols. Results are from a single experiment in triplicate. Each experiment was repeated at least 3 times with similar results.

An alkaline pH increases the activity of individual ASL antimicrobial peptides and their synergistic interactions (Abou Alaiwa M H, Reznikov L R, Gansemer N D, Sheets K A, Horswill A R, Stoltz D A, et al. pH modulates the activity and synergism of the airway surface liquid antimicrobials beta-defensin-3 and LL-37. Proceedings of the National Academy of Sciences of the United States of America. 2014; 111(52):18703-8. doi: 10.1073/pnas.1422091112. PubMed PMID: 25512526; PubMed Central PMCID: PMC4284593). Therefore, the effect of tromethamine on hBD-3 and LL-37 antimicrobial activity was tested. a bioluminescence-based assay was used in which *S. aureus* Xen29 was modified to express luminescence genes. Compared to an iso-osmolar non-ionic control (pH=7.02), tromethamine (pH=8.65) enhanced antimicrobial activity of both hBD-3 (FIG. 4A) and LL-37 (FIG. 4B). These data suggest that increasing pH independently of $HCO_3^-$ concentration enhances hBD-3 and LL-37 antimicrobial activity.

Tromethamine Increases the pH of Tracheal ASL in CF Piglets and Enhances Bacterial Killing To investigate whether tromethamine produces a prolonged increase in tracheal ASL pH, tromethamine was aerosolized onto the airways of non-CF piglets. Tromethamine raised pH immediately after administration (FIG. 5A). While the effect of $HCO_3^-$ on ASL returned to baseline by 30 minutes (FIG. 2A), the effect of tromethamine was still higher than baseline at 60 minutes (FIG. 5A). Whether aerosolized tromethamine rescues the bacterial killing defect in CF piglets was also tested. The mucosal surface of airways in newborn CF piglet was exposed via a small tracheal widow and aerosolized tromethamine. ASL pH and bacterial killing was measured 15 minutes after administration of tromethamine or NaCl as a control. Tromethamine increased pH (FIG. 5B) and enhanced bacterial killing compared to NaCl (FIG. 5C). The increase in bacterial killing was more pronounced compared to what was found in CF sputum, perhaps because the antimicrobial factors in CF sputum may have been inactivated by proteases, thereby limiting the killing capacity of sputum when compared to ASL. Thus, these data suggest that tromethamine increases ASL pH in a sustained manner and it corrects the bacterial killing defect seen in CF pigs.

Tromethamine Increases Human Nasal pH and the Effect is Prolonged

To examine whether tromethamine could also provide a long-lasting buffering effect in human airways, the effect of acute tromethamine administration on nasal pH was tested. Aerosolized tromethamine alkalinized the nasal pH of healthy human subjects, with the effect lasting at least two hours (FIG. 6A). Administration of an isoosmolar solution of xylitol, a non-ionic sugar, had no effect on nasal pH (FIG. 6B). These findings are similar to the effect of tromethamine on tracheal ASL pH in pigs. The effect of tromethamine on nasal pH in individuals with CF during one of their clinic visits was also investigated. In the clinic setting, pH measurements could only be obtained 30 minutes after drug administration. Aerosolization of 250 μl tromethamine increased nasal pH for 30 minutes, the total duration of the experiment (FIG. 6C). Disruption of epithelial integrity in the nasal epithelia could lead to serum leakage and increase pH to serum levels. The high transepithelial nasal voltage seen in CF patients requires an intact epithelia. It was found that tromethamine had no effect on nasal voltage (FIG. 6D). Thus tromethamine appears to produce no disruption of the epithelial barrier integrity and increase in pH are likely secondary to a direct buffering effect on ASL.

Tromethamine in Combination with Hypertonic Saline (7% NaCl) Increases CF Sputum pH and Enhances Bacterial Killing Hypertonic saline is often used in individuals with advanced CF airways disease to accelerate mucociliary transport (Donaldson S H, Bennett W D, Zeman K L, Knowles M R, Tarran R, Boucher R C. Mucus clearance and lung function in cystic fibrosis with hypertonic saline. The New England journal of medicine. 2006; 354(3):241-50. doi: 10.1056/NEJMoa043891. PubMed PMID: 16421365; Elkins M R, Robinson M, Rose B R, Harbour C, Moriarty C P, Marks G B, et al. A controlled trial of long-term inhaled hypertonic saline in patients with cystic fibrosis. The New England journal of medicine. 2006; 354(3):229-40. doi: 10.1056/NEJMoa043900. PubMed PMID: 16421364).

Figures 7A, 7B:
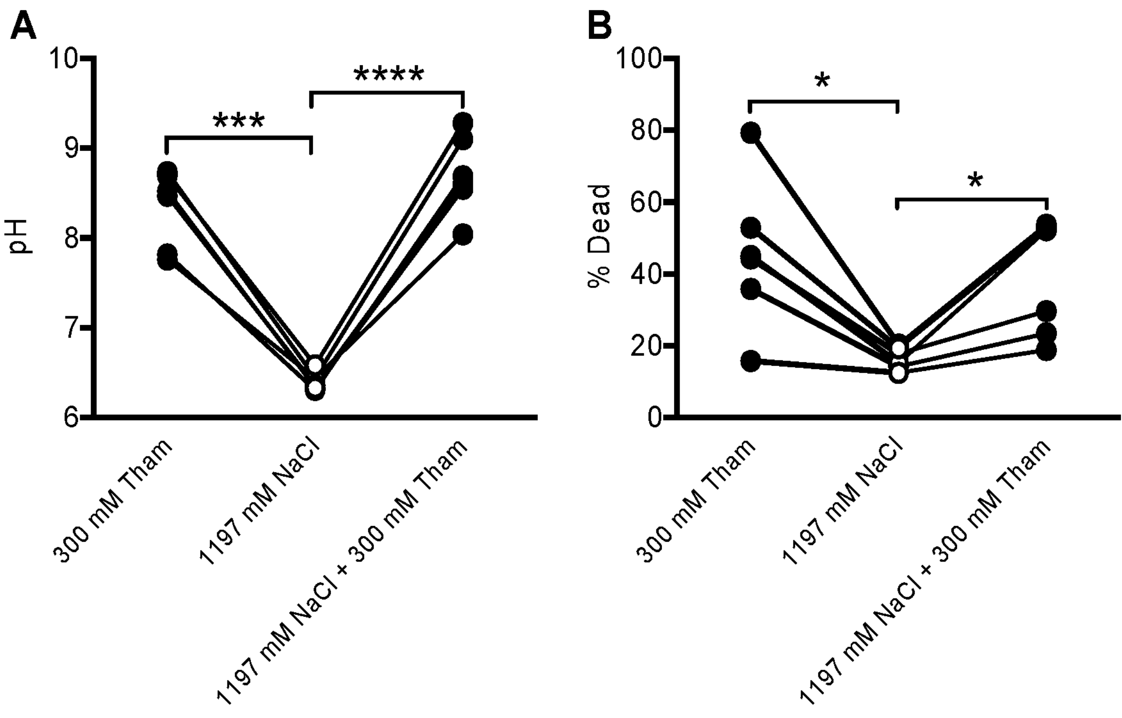
FIGS. 7A-7B. Antimicrobial activity of sputum from subjects with cystic fibrosis (CF). Data are pH and antimicrobial activity of CF sputum mixed at 1:1 (v/v) with 300 mM Tham, 1197 mM NaCl, or a combination of 1197 mM NaCl/300 mM Tham. A. CF sputum pH. B. CF sputum antimicrobial activity. Each data point indicates sputum from a different donor. N=6, One-way ANOVA with Holm-Sidak's Multiple Comparison Test. *<0.05, *<0.005, **<0.001.
Figures 8A, 8B, 8C, 8D:
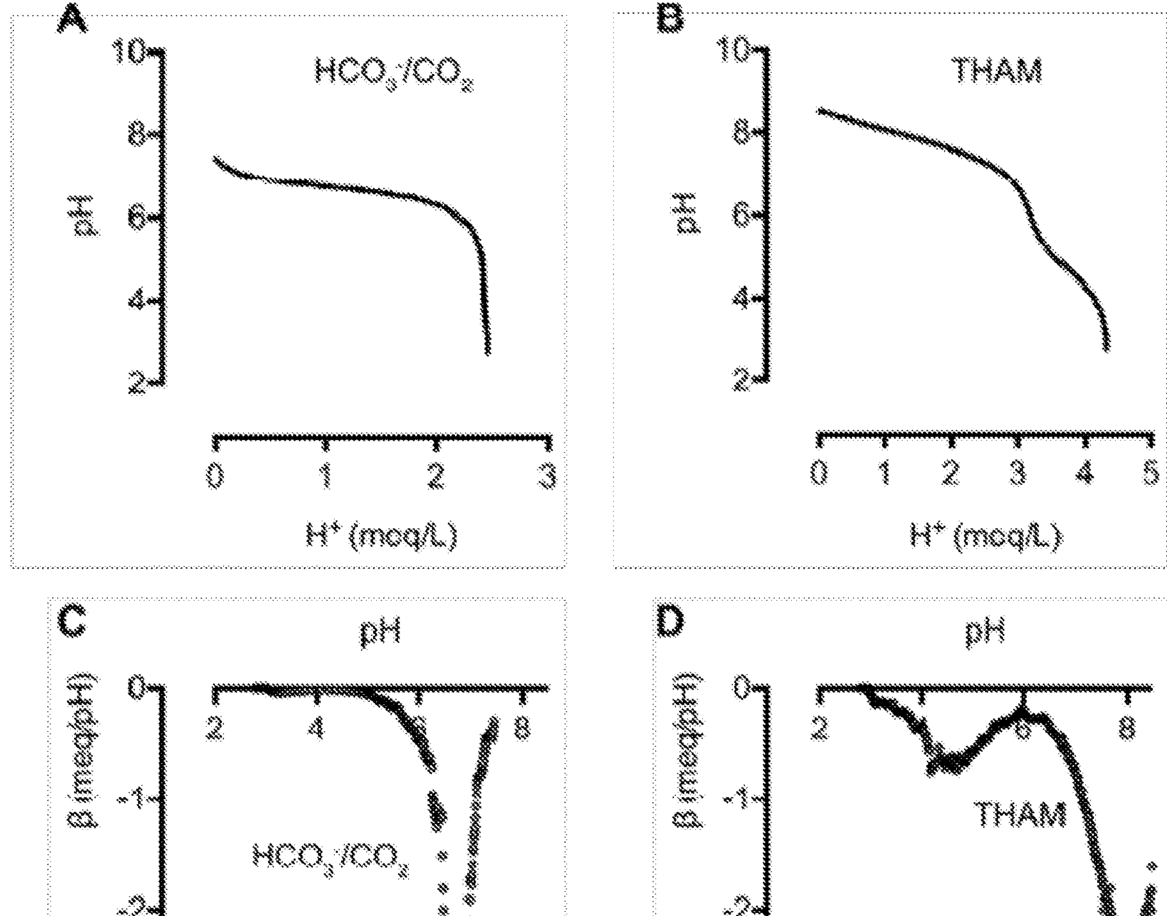
FIG. 8A-8D. Buffering capacity of $HCO_3^-$/$CO_2$ buffer and tromethamine. (A and B) Data are acid titration curves and represent drop in pH after addition of acid. A. $HCO_3^-$/ $CO_2$ and B. tromethamine. (C and D) amount of acid (in meq) needed to drop pH by 1 unit or buffering capacity (β)

However, it has been reported that salt inhibits individual antimicrobial peptides and their synergistic interactions. Because tromethamine may be useful as a primary or adjunct inhalational therapy, it was asked whether tromethamine would increase pH in the presence of hypertonic saline, and whether a mixture of tromethamine and hypertonic saline would enhance bacterial killing. Sputa was collected from CF subjects and mixed it in a 1:1 (w/v) dilution of tromethamine (300 mM), hypertonic saline (1197 mM, 7% NaCl) or a combination of tromethamine (300 mM) and hypertonic saline (1197 mM, 7% NaCl). Compared to hypertonic saline or isotonic saline (in FIG. 1), tromethamine alone or in combination with hypertonic saline raised the pH of CF sputum (FIG. 7A). Similar to the effect of $HCO_3^-$ on CF sputum (FIG. 1), tromethamine alone or in combination with hypertonic saline, increased the ability of CF sputum to kill *S. aureus* compared to hypertonic saline alone (FIG. 7B). Although there was a tendency for lower bacterial killing with tromethamine and hypertonic saline in combination in comparison to tromethamine alone, the difference was not statistically significant. Thus, tromethamine alone or in combination with hypertonic saline is effective at increasing ASL pH and reversing the bacterial killing defect in CF sputum.

Discussion

Loss of the CFTR anion channel reduces ASL pH. The present results suggest that both $HCO_3^-$ and tromethamine increase ASL pH in pigs and humans with CF. However, tromethamine increased ASL pH for a longer duration than $HCO_3^-$. Tromethamine also enhanced ASL bacterial killing in pig airways and human CF sputum. Thus, increasing ASL pH with tromethamine enhances host defense and thereby benefits people with CF.

The surface of the airways lies in proximity with the environment and is constantly exposed to microorganisms. The liquid covering the airways contains a plethora of cationic antimicrobial factors that form the first line of defense against invading bacteria. It has been shown that an abnormally acidic ASL inhibits the activity of individual antimicrobial factors and their combined synergistic interaction. Yet, whether the contribution of pH-mediated antimicrobial factor inhibition is $HCO_3^-$-dependent has been uncertain. Here, it is shown that both in the presence and absence of $Ca^{2+}$, $HCO_3^-$ did not increase cationic peptide bacterial killing when pH was constant. On the contrary, there was a small inhibition. This result suggested that pH buffers other than $HCO_3^-$, such as tromethamine, might increase ASL antimicrobial activity.

In the present experiments, an FDA approved intravenous buffer was identified that can be used as an aerosol to alkalinize the ASL of CF airways. Tromethamine is a biologically inert weak amine base with an elimination half-life of 16 to 48 hours after intravenous administration (Brasch H, Thies E, Iven H. Pharmacokinetics of TRIS (hydroxymethyl-)aminomethane in healthy subjects and in patients with metabolic acidosis. Eur J Clin Pharmacol. 1982; 22(3):257-64. PubMed PMID: 7106159). In addition to intravenous usage, tromethamine is included as an expedient in many topical, injectable, and/or inhalational FDA approved drugs. Both Iloprost inhalation solution (Ventavis®) and nasal Ketorolac tromethamine (SPRIX®) are formulated with Tromethamine with a safe toxicological profile. Similar to its effect on pH in the serum, in the airways tromethamine may alkalinize the ASL by buffering protons. In the serum of patients with acidosis, tromethamine is protonated. Because protonated tromethamine is cell impermeable, cellular absorption is reduced and as a result, the effect on serum pH is sustained.

Loss of CFTR reduces airway epithelial $HCO_3^-$ secretion, diminishes ASL pH, and interferes with at least two important host defenses: antibacterial activity and mucociliary transport. Each defect may independently contribute to lung disease in CF. Treating people with cystic fibrosis with antibiotics improves their clinical status, without correcting the mucus abnormalities. Accordingly, inhaled tromethamine might be beneficial even it only corrects the antimicrobial defect. While increasing ASL pH will change the viscoelastic properties of CF mucus, it was unclear whether such changes in pH and viscosity would enhance MCT.

The present data show that tromethamine increases sputum pH and improves bacterial killing even in the presence of hypertonic saline. A combination of tromethamine and hypertonic saline is of therapeutic benefit in CF airways.

Methods

CF Sputum Preparation

Adults diagnosed with CF were recruited. Patients were asked to swallow saliva and to expectorate all secretions during routine clinic visits. Sputum plugs were visually identified and separated from saliva, weighed and stored at −70° C. in small, tightly sealed containers to minimize water loss under needed. Sputum was mixed in a 1:1 v/v with either 200 mM NaCl, 200 mM $NaHCO_3$, 1197 mM NaCl, 300 mM tromethamine, or 1197 mM NaCl/300 mM tromethamine. To guarantee adequate mixing of sputum with the different solutions, the mixture was homogenized (Sonic Dismembrator Model 100, Fisher Scientific) for 30 seconds. All experiments were conducted in a humidified chamber with constant 5% $CO_2$.

pH Measurements

To measure nasal pH, a Sandhill ZepHr PHNS-P (Sandhill Scientific, Highlands Ranch, CO) Mobidium pH probe was used with an internal reference electrode as previously described (Abou Alaiwa M R, Beer A M, Pezzulo A A, Launspach J L, Horan R A, Stoltz D A, et al. Neonates with cystic fibrosis have a reduced nasal liquid pH; A small pilot study. Journal of cystic fibrosis: official journal of the European Cystic Fibrosis Society. 2014; 13(4):373-7. doi: 10.1016/j.jcf.2013.12.006. PubMed PMID: 24418186; PubMed Central PMCID: PMC4060428). Prior to each study the pH probe was calibrated in buffer solutions of pH 6, 7 and 8 (VWR, West Chester, PA). Voltage was recorded with an Oakton pH6+ meter (Cole-Palmer, Vernon Hills, IL) and corrected to temperature. The probe was positioned at 6 cm from the most caudal aspect of the columella. The probe remained in position until the readings were stable. All measurements were taken from the right nostril and by the same operator. Subjects on intranasal medications (steroids or anticholinergics) or with history of nasal or sinus surgery were excluded from the study. Adverse events including nasal congestion or epistaxis were collected but none reported.

To measure pH in sputum, a needle-type fiber optic pH meter (World Precision Instruments) was used (Pezzulo A A, Tang X X, Hoegger M J, Alaiwa M H, Ramachandran S, Moninger T O, et al. Reduced airway surface pH impairs bacterial killing in the porcine cystic fibrosis lung. Nature. 2012; 487(7405):109-13. Epub 2012/07/06. doi: 10.1038/nature11130. PubMed PMID: 22763554; PubMed Central PMCID: PMC3390761). The pH meter was calibrated before each set of measurements using standard pH buffer solutions. All measurements were obtained in a humidified chamber at 37° C. and constant 5% $CO_2$ to mimic physiologic conditions.

To measure pH in pigs in vivo, non-invasive dual lifetime referencing was used to interrogate a 3×3 mm planar optode (pH sensitive foil, PreSens GmbH) applied directly to the tracheal surface of anesthetized pigs (Pezzulo A A, Tang X X, Hoegger M J, Alaiwa M H, Ramachandran S, Moninger T O, et al. Reduced airway surface pH impairs bacterial killing in the porcine cystic fibrosis lung. Nature. 2012; 487(7405):109-13. Epub 2012/07/06. doi: 10.1038/nature11130. PubMed PMID: 22763554; PubMed Central PMCID: PMC3390761). pH-dependent polarized light phase shift was measured using a single channel pH meter (pH-1 mini; PreSens GmbH). The tip of the fiber optic pH meter was kept at the same constant distance from the tracheal surface in all samples and confirmed by recording the amplitude. Calibration before each set of measurements was done by measuring phase shift from flat filters soaked in standard pH buffers. All measurements were obtained in a humidified chamber at 37° C. and constant 5% $CO_2$ to mimic physiologic conditions.

Nasal Voltage (Vt) Measurements

Nasal voltage measurements obtained in subjects with CF after tromethamine administration according to the description by Solomon et al. (Solomon G M, Konstan M W, Wilschanski M, Billings J, Sermet-Gaudelus I, Accurso F, et al. An international randomized multicenter comparison of nasal potential difference techniques. Chest. 2010; 138(4): 919-28. doi: 10.1378/chest.10-0179. PubMed PMID: 20472865; PubMed Central PMCID: PMCPMC2951758) with Electronic Data Capture (ADInstruments), KCl calomel electrodes (Thermo Fischer Scientific Inc), and 3% agar nasal catheter and reference bridges (Rowe S M, Clancy J P, Wilschanski M. Nasal potential difference measurements to assess CFTR ion channel activity. Methods Mol Biol. 2011; 741:69-86. doi: 10.1007/978-1-61779-117-8_6. PubMed PMID: 21594779; PubMed Central PMCID: PMCPMC3760477).

Methods for Measuring Buffering Capacity of $HCO_3^-$ and Tromethamine

An automated endpoint titration was carried out using Titralab® 856 workstation (Radiometer Analytical). pH was measured using calomel combined pH electrode (pHc4000, Radiometer Analytical). 100 mM HCl was delivered into 5 mL of buffer at a rate of 0.2 ml/min. Titration was carried out to endpoint of pH 3. The volume of HCl delivered was recorded and used to calculate the acid equivalents needed to raise pH by 1 unit or buffering capacity.

Methods for Administering $HCO_3^-$ or Tromethamine

To alter tracheal pH in pigs using $HCO_3^-$ or tromethamine, the solutions were aerosolized to the exposed tracheal surface as previously described (Pezzulo A A, Tang X X, Hoegger M J, Alaiwa M H, Ramachandran S, Moninger T O, et al. Reduced airway surface pH impairs bacterial killing in the porcine cystic fibrosis lung. Nature. 2012; 487(7405):109-13. Epub 2012/07/06. doi: 10.1038/nature11130. PubMed PMID: 22763554; PubMed Central PMCID: PMC3390761). Pigs were initially sedated with Ketamine (20 mg/kg, IM injection) and Xylazine (2 mg/kg, IM injection) and anesthetized using Propofol (2 mg/kg, IV injection). The trachea was surgically exposed and accessed anteriorly. A small anterior window through the tracheal rings accessed a tracheal window to interventions and pH measurements. All studies obtained in a 100% humidified chamber at 37° C. and constant 5% $CO_2$ to mimic physiologic conditions.

To change nasal pH in human nostrils, tromethamine was administered intra-nasally using a 250 μl preloaded Accuspray syringe (Becton Dickinson Pharmaceutical Systems, Franklin Lakes, NJ) (Abou Alaiwa M H, Beer A M, Pezzulo A A, Launspach J L, Horan R A, Stoltz D A, et al. Neonates with cystic fibrosis have a reduced nasal liquid pH; A small pilot study. Journal of cystic fibrosis: official journal of the European Cystic Fibrosis Society. 2014; 13(4):373-7. doi: 10.1016/j.jcf.2013.12.006. PubMed PMID: 24418186; PubMed Central PMCID: PMC4060428).

Bacterial Killing Assays

To interrogate individual bacteria killing in CF sputum or in pigs, bacteria-coated grids assay were used (Pezzulo A A, Tang X X, Hoegger M J, Alaiwa M H, Ramachandran S, Moninger T O, et al. Reduced airway surface pH impairs bacterial killing in the porcine cystic fibrosis lung. Nature. 2012; 487(7405):109-13. Epub 2012/07/06. doi: 10.1038/nature11130. PubMed PMID: 22763554; PubMed Central PMCID: PMC3390761; Abou Alaiwa M H, Reznikov L R, Gansemer N D, Sheets K A, Horswill A R, Stoltz D A, et al. pH modulates the activity and synergism of the airway surface liquid antimicrobials beta-defensin-3 and LL-37. Proceedings of the National Academy of Sciences of the United States of America. 2014; 111(52):18703-8. doi: 10.1073/pnas.1422091112. PubMed PMID: 25512526; PubMed Central PMCID: PMC4284593). Gold grids (200 mesh, Ted Pella) were functionalized using a series of intervention: 100 mM 11-mercaptoundecanoic acid (MUA in 100% alcohol, Aldrich) for 60 min at room temperature, 1:1 mixture of 100 mM N-ethyl-N-(3-diethylaminopropyl) carbodiimide) (EDC) and 100 mM N-hydroxysuccinimide (NETS) for 30 min at room temperature, 0.1 mg/ml Neutravidin (Sigma) at 37° C. for 1 hour.

Two different strains of *S. aureus* were used (SH1000 a human strain for CF sputum killing studies and SA43 a porcine strain for pig studies). Bacteria were grown to mid-log phase, incubated with 0.2 mg/ml N-hydroxysulphosuccinimide (sulpho-NHS)-biotin for 60 min at room temperature, quenched with 100 mM glycine to bind excess free biotin and allowed to attach to Neutravidin-coated grids for 15 minutes prior to the experiment.

After bacteria-coated grids were exposed to pig trachea for 5 minutes or CF sputum for 15 minutes, they were immediately rinsed in phosphate buffered saline and stained with SYTO9/propidium iodide (Live/Dead BacLight Bacterial viability assay, Invitrogen), mounted on slides and imaged on a laser-scanning confocal microscope (Olympus FV1000). Live (green) and dead (red) bacteria were automatically counted using Image-based Tool for Counting Nuclei (ITCN 1.6, UCSB Center for Bio-Image Informatics, UC San Barbara) an ImageJ (U.S. National Institutes of Health, Bethesda, Maryland, USA) plugin.

Antimicrobial Factors and Luminescence Antibacterial Assay

ASL antimicrobial factors included recombinant human beta-defensin-3 hBD-3 (Peprotech, Rocky Hill, NJ) and human LL-37 (Anaspec, Fremont, CA). Cationic peptides were dissolved in acidified water (0.01% acetic acid) that contained 0.1% bovine serum albumin (BSA).

*Staphylococcus aureus* Xen-29 (Caliper LifeSciences Bioware™, Hopkinton, MA) was used. *S. aureus* Xen-29 was derived from *S. aureus* 12600, a pleural fluid isolate, which is also designated as NCTC8532. *S. aureus* Xen-29 possesses a stable copy of the modified *Photorhabdus luminescens* luxABCDE operon at a single integration site on the bacterial chromosome. For maintenance of luminescence, the bacteria were grown in TSB in the presence of kanamycin (10 μg/ml).

Antimicrobial peptide activity was tested in a buffer composed of 1% Tryptic Soy Broth (TSB) (Casein peptone 17 g/l, Soya peptone 3 g/l, NaCl 5 g/l, $K_2HPO_4$ 2.5 g/l, Glucose 2.5 g/l) and supplemented with 10 mM potassium phosphate buffer with pH adjusted by varying the ratio of monobasic to dibasic phosphate and 100 mM NaCl to achieve an ionic strength of 125 mM.

Bacteria were grown overnight at 37° C. in medium described above, diluted 1:100, and grown to exponential phase. Bacteria were harvested by centrifugation and suspended in the 1% TSB buffer. Bacteria ($5\times10^4$ CFU) were incubated with antimicrobial factors in a 96-well plates (Optiplate; Packard Instruments, Meriden, CT) in a total volume of 120 μl. Luminescence was measured with a luminometer (Spectra Max L, Molecular Devices, Sunnyvale, CA) and reported as relative light units (RLU). A previous study determined that reductions in luminescence have an excellent correlation with a decrease in CFU (Travis S M, Conway B A, Zabner J, Smith J J, Anderson N N, Singh P K, et al. Activity of abundant antimicrobials of the human airway. American journal of respiratory cell and molecular biology. 1999; 20(5):872-9. Epub 1999/05/05. PubMed PMID: 10226057). All experiments included control bacteria that did not receive antimicrobials, but were incubated in buffer of identical ionic strength and pH. Data are shown as relative luminescence as a percentage of control (RLU % control).

Preparation of Isohydric (Same pH) Solutions

To test antimicrobial peptide activity under the same pH conditions and increasing concentrations of $HCO_3^-$, four solutions were used all adjusted to the same pH of 7.5 and same ionic strength (~161 mM in the presence of $CaCl_2$ or $MgSO_4$ and ~154 mM in the absence of $CaCl_2$ or $MgSO_4$) and supplemented with 1% TSB. To test the effect of increasing $HCO_3^-$ concentrations at the same pH in the absence of calcium or magnesium, the same four solutions were used without the addition of $CaCl_2$ or $MgSO_4$:

10 mM $NaHCO_3$: NaCl 140 mM, KCl 3 mM, $CaCl_2$ 1 mM, $NaHCO_3$10 mM, $NaH_2PO_4$ 1.25 mM, $MgSO_4$ 1 mM, D-glucose 10 mM, $CO_2$ 2%.

26 mM $NaHCO_3$: NaCl 124 mM, KCl 3 mM, $CaCl_2$ 1 mM, $NaHCO_3$26 mM, $NaH_2PO_4$ 1.25 mM, $MgSO_4$ 1 mM, D-glucose 10 mM, $CO_2$ 5%.

50 mM $NaHCO_3$: NaCl 100 mM, KCl 3 mM, $CaCl_2$ 1 mM, $NaHCO_3$50 mM, $NaH_2PO_4$ 1.25 mM, $MgSO_4$ 1 mM, D-glucose 10 mM, $CO_2$ 9%.

80 mM $NaHCO_3$: NaCl 70 mM, KCl 3 mM, $CaCl_2$ 1 mM, $NaHCO_3$80 mM, $NaH_2PO_4$ 1.25 mM, $MgSO_4$ 1 mM, D-glucose 10 mM, $CO_2$ 12%.

Animals

Both female and male newborn pigs were studied with targeted disruption of the CFTR gene $CFTR^{-/-}$, generated from mating $CFTR^{+/-}$ pigs. The wild-type littermates were also studied. All pigs were obtained from Exemplar Genetics.

Statistics

Data are presented as points from individual humans or animals or sputum samples obtained from individual donors with mean±SEM indicated by bars. For statistical analysis, a Wilcoxon signed-rank test or a Wilcoxon-Mann-Whitney test were used to compare two groups and a 1-way ANOVA for multiple comparisons. In FIGS. 7 (A and B) and 6 C, Holm-Sidak's Multiple Comparison Test was used for pairwise differences in pH or bacterial killing. Differences were considered statistically significant at $P<0.05$.

Example 2

Cystic fibrosis (CF), the most common life-shortening recessively inherited disease, affects ~30,000 Americans, and is associated with significant healthcare costs. CF is caused by mutations in the gene that encodes the cystic fibrosis transmembrane conductance regulator (CFTR), a $HCO_3^-$ and $Cl^-$ anion channel. Airway infection, mucus accumulation, and inflammation occur early, oftentimes within weeks to months after birth. Despite earlier diagnosis and new therapeutic options, treatments for the disease remain suboptimal and CF continues to shorten lives.

Airways use multiple mechanisms to protect lungs against infection. One important defense is the complex soup of antimicrobial peptides, proteins, and lipids in airway surface liquid (ASL). Another is mucociliary transport (MCT), which traps invading pathogens in mucus that are then propelled up the airways by cilia. It is now known that both of these mechanisms are impaired in newborn CF pigs that over time develop airway disease similar to human CF. The molecular mechanism for these defects involves abnormal $HCO_3^-$ secretion due to loss of CFTR function. These two defects may have synergistic effects on disease severity. For example, patients with primary ciliary dyskinesia have impaired MCT only, but have a milder phenotype than people with CF. Thus, correcting even one host defense defect might be beneficial and improving most defense defects could perhaps delay or prevent the progression of CF lung disease.

Informed by knowledge of the molecular mechanisms of host defense defects in CF, a novel therapeutic intervention is developed that targets the common defect that impairs these two defense mechanisms: acidic ASL pH. THAM (tromethamine) is an alkalinizing agent, with a long serum half-life, used intravenously to treat metabolic acidosis. Inhaled THAM: (1) alkalinizes ASL with a longer half-life than $NaHCO_3$, (2) corrects pH-related antimicrobial killing defects, and (3) reverses CF mucus abnormalities.

CF Airways have an Acidic ASLpH.

Loss of CFTR-dependent $HCO_3^-$ secretion reduces ASL pH. This response has been reported in humans and pigs, and under in vitro, ex vivo, and in vivo conditions. ASL pH is reduced in newborn pigs with CF (FIG. 10A), in human infants with CF (FIG. 10B), and in submucosal gland secretions from CF children. ASL pH is also more acidic in CF human and pig airway cultures. Similar findings have been reported in adults with CF, although the data have been more variable. It is not known if it is the secondary effects of infection, inflammation, and airway remodeling on ASL pH that causes the variable CF:non-CF differences in adults.

An Acidic ASL pH Impairs Airway Host Defense.

Figures 11A, 11B, 11C, 11D, 11E, 11F:
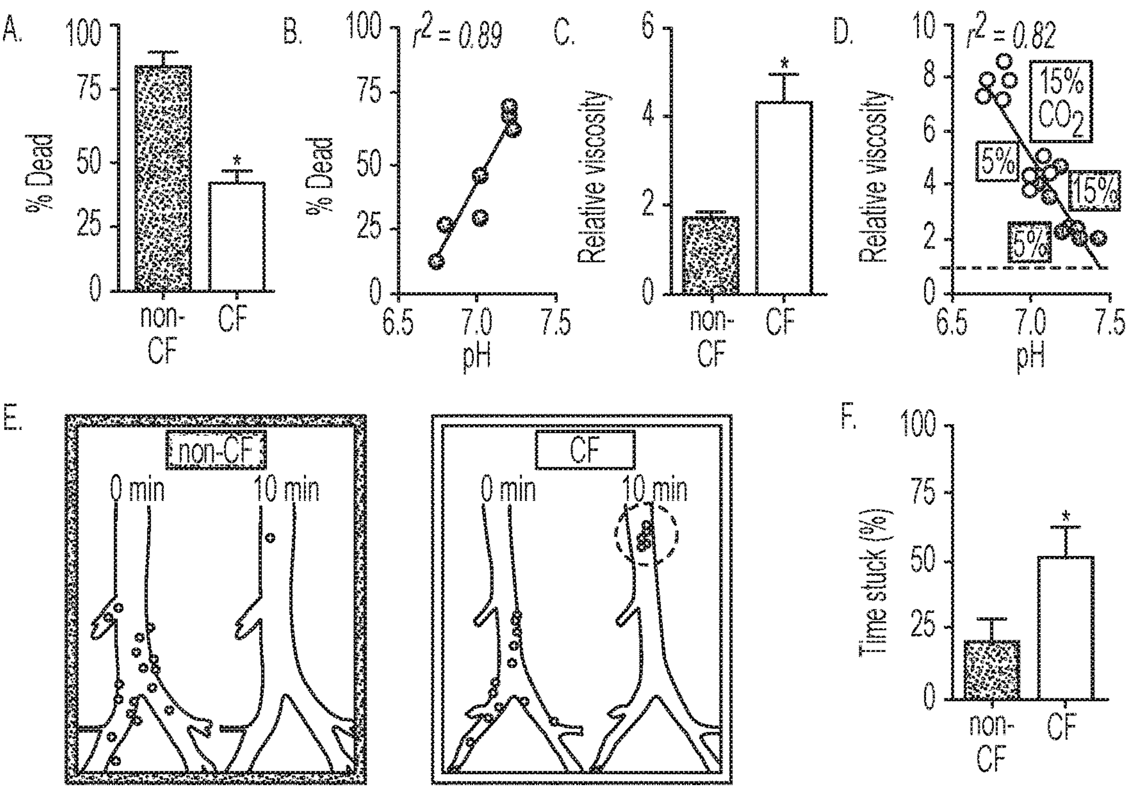

In humans and pigs lacking CFTR-dependent $HCO_3^-$ secretion, unchecked $H^+$ secretion by the non-gastric $H^+/K^+$ ATPase (ATP12A) acidifies ASL, and the acidic ASL pH impairs at least two important host defenses: (1) ASL antimicrobial factors. The acidic pH inhibits the individual and synergistic activities of antimicrobial factors, so that small changes in pH cause large defects in bacterial killing (FIGS. 11A&B); and (2) Mucociliary transport (MCT). CF piglet mucus was more viscous than non-CF, due to reduced ASL pH (FIG. 11C). Small changes in pH also have significant effects on mucus viscosity (FIG. 11D) and likely have important consequences for proper MCT. With a novel CT scan-based MCT assay, small radiopaque microdisks were used as tracers and it was observed that in CF, following methacholine treatment, the number of immobile or "stuck" microdisks was increased (FIGS. 11E&F). MCT was hindered, in part, because mucus strands originating from CF submucosal gland ducts failed to detach from the duct openings. In contrast to human and pig airways, mouse airways expressed little ATP12A and secreted minimal $H^+$;

consequently, CF and non-CF mice ASL had similar pH and host defenses were intact. Expressing ATP12A in CF mouse airways acidified ASL, impaired defenses, and increased airway bacteria. This data suggest that reduced ASL pH is a key abnormality that initiates CF airway disease.

$NaHCO_3$ and THAM Alkalinize the Airway and Restore Host Defenses.

It has been shown that Na—$HCO_3$ raises ASL pH, but the effect is short-lived (FIG. 12). Aerosolized THAM, a tris-based, non-$HCO_3^-$ buffer, also raises ASL pH but the effect is longer-lasting (FIG. 12). By increasing pH, both $NaHCO_3$ and THAM (FIGS. 13A&B) reduced viscosity and improved bacterial killing to non-CF levels. The pH effects occur with very small pH changes (≤0.1 units). Thus, raising ASL pH even in non-CF enhances host defense (FIGS. 11B&D).

THAM is Safe.

The data suggest that THAM is safe as an alkalinizing agent. THAM is FDA approved and has a long record of safe intravenous usage in critically ill humans to reverse metabolic acidosis. THAM is used as an excipient for inhaled prostacyclin and nasal ketorolac. Human subjects reported no adverse effects 24 h after aerosolized nasal delivery of THAM. THAM exposure in mice is well tolerated. THAM aerosolization raised the airway pH (FIG. 14A), and no adverse treatment related findings were observed in clinical signs, gross pathology, BAL cell counts/cytokines/LDH, bronchoconstriction, or histopathology (FIGS. 14B-G).

Overview of Experimental Approaches and General Study Designs.

Animal Studies.

Non-CF and CF pigs are randomly assigned to treatment group and, unless otherwise stated, male and female pigs are studied. THAM inhalation: In awake, non-sedated pigs, THAM (commercial solution, pH 8.6, 0.3 M, Hospira, Lake Forest, IL) or control solution (commercial 0.9% saline, Baxter Health Care, Mundelein, IL) is delivered via a PARI LC-PLUS® nebulizer, using a soft cone mask over the snout, (1 ml over 10 min). Pigs tolerate the cone mask well without sedation or restraint. Saline was chosed as the control because it has a close osmolarity to THAM, saline is commonly used as a control inhaled solution in CF studies, and aerosolized saline had no effect on human nasal ASL pH. pH: For tracheal ASL pH measurements, either dual lifetime referencing is used to interrogate a pH sensitive foil (planar optode & pH-1 mini pH meter, PreSens GmbH) applied directly to the tracheal surface of anesthetized pigs with a tracheal window or a Sandhill ZepHr PHNS-P esophageal pH probe (Sandhill Scientific, Highlands Ranch, CO) placed directly on the airway surface (nose and trachea).

Human Studies.

Nasal aerosolization: Control or THAM solutions, similar to above, are nebulized onto the nasal epithelium (250 μl) using an Accuspray syringe (Becton Dickinson Pharmaceutical Systems, Franklin Lakes, NJ). Nasal ASL pH: The Sandhill probe is used. Study assignment and general protocols: Subjects are blinded to treatment. THAM/control solution syringes are identical. Humans are randomly assigned to study group. Subjects: Non-CF and CF (evidence of CFTR mutations, positive sweat Cl-test, and ≥1 clinical CF finding) and age 16 or older, who are able to provide written informed consent, are enrolled. Inclusion criteria for CF subjects: FEV1%>35%, $O_2$ saturation >90% on room air, and clinically stable. Exclusion criteria: Pregnancy, tobacco use, recreational drug use, use of any investigational study drug within 30 days, or clinical findings consistent with a CF pulmonary exacerbation or flare up of seasonal allergic rhinitis. No use of antibiotics (oral or nasal), steroid, or topical intranasal preparation within 14 d period prior to study initiation.

Statistical Overview and Sample Size Determination.

All analyses are run using R or SAS 9.4 software (SAS Institute, Cary, NC) and at a 5% significance level. Differences are analyzed using 2 sample t-test, Wilcoxon signed rank test, and analysis of variance (ANOVA) as indicated. When able, comparisons are made both pair-wise (change from baseline) as well as between groups. Since human subjects receive the treatment and control it is possible to match on subject. Main outcomes are analyzed using a generalized linear mixed modeling with a random effect for subject and link function as determined by Akaike's information criterion (AIC). The sample sizes were chosen (alpha 0.05, and power 0.8) based upon available preliminary data as values of variability.

Duration of THAM-Induced ASL Alkalinization in Non-CF and CF Airways

It was reported that aerosolized $NaHCO_3$ and THAM raise the ASL pH, but that THAM's alkalinizing effects are longer-lived (FIG. 12). The data (FIGS. 12&15A) suggest that THAM might cause a greater alkalinization in CF due to a lower baseline ASL pH and THAM's buffering capacity at a low pH. Inhaled THAM has a greater and more prolonged alkalinizing effect on ASL pH in CF airways.

Pig Studies.

Non-CF and CF newborn pigs (n=6/group) receive aerosolized control or THAM. Nasal and tracheal pH are measured 1) continuously for 2 h in sedated pigs with a pH probe in their right nare and another passed through their vocal cords into their trachea (FIG. 16), and 2) in another cohort of pigs at 6 and 12 h after aerosolization. Prior to euthanasia, tracheal pH is measured with the pH-sensitive foil.

Human Studies.

A randomized, double-blinded, cross-over study (THAM followed by saline or saline followed by THAM) is used. Non-CF and CF human subjects (n=16/group) receive aerosolized solutions to nasal epithelia. Continuous nasal pH readings are obtained (for 12 h) (section 3.5). This procedure is well-tolerated and similar to 24 h esophageal probe pH tests in humans. Subjects return 14 d later, repeat the nasal pH testing to confirm washout, and then repeat the study with the opposite solution. End-points. End-points are peak pH response, area under the pH curve, recovery time to baseline pH values, and duration of time that ASL pH remains 0.2 units above baseline after THAM. 0.2 units was chosen because this is twice the pH change that affects the host defense defects that we study (FIGS. 11B&D).

Interpretation.

Similar to in serum, THAM becomes protonated, alkalinize the ASL, and generate $HCO_3^-$. The data suggest that 30 min after THAM aerosolization into the nose of people with CF the pH change was ~80% of the maximal pH response, compared to 30% in non-CF noses (FIG. 12). This suggests that, as THAM generates $HCO_3^-$ in the ASL, CFTR-mediated absorption may shorten the duration of alkalinization in non-CF airways (FIG. 13B). Thus, in the absence of CFTR, THAM's effects could be prolonged (FIG. 15B), although other mechanisms could also contribute including altered non-CFTR acid-base transporters, THAM clearance, or differences in buffering capacity.

Airway Alkalinization Enhance Bacterial Eradication in CF Pigs

Soon after birth, the lungs of CF pigs become colonized with bacteria, and over weeks they develop chronic infection like humans. Previous data indicate that lack of CFTR function reduces the effectiveness of at least two defenses: ASL antimicrobial activity and MCT, which normally eradicate bacteria from the lungs. The combination of bacterial killing and clearance results in bacterial eradication from the lungs. The grey box shows a simplified model that does not take into account bacterial attachment/growth, biofilm formation, immune cells, etc. However, for the purpose of this aim, it should be helpful to define the terms.

| bacterial killing | + | bacterial clearance | = | bacterial eradication |
|---|---|---|---|---|

The effect of THAM on ASL antimicrobial activity (bacterial killing) and bacterial clearance is investigated by MCT. It has be found tht THAM can improve both bacterial killing (FIG. 13B) and modify the viscoelastic properties of mucus in CF ASL (FIG. 13A), suggesting it may also improve bacterial clearance by mucociliary transport. These data suggest that THAM is a novel therapeutic approach for CF airway disease.

Experimental Procedure.

To investigate if inhaled THAM improves ASL microbial eradication in CF pigs, a variety of novel approaches are used that complement each other. General approach: Newborn non-CF and CF pigs are used. Two treatment groups: control and THAM (section 3.5), n=8/group. Three approaches are used to test if THAM enhances bacterial eradication. Approaches #1 and #2 measure a combination of bacterial killing and other factors leading to bacterial eradication, such as clearance by MCT. Approach #3 directly measures bacterial killing.

Approach #1: Bacterial challenge. Newborn CF pigs fail to eradicate *S. aureus* after a pulmonary challenge. Pigs receive control or THAM solutions. Initially, bacteria killing is tested at 0, 1.5 h, and 6.5 h following aerosolization. An intrapulmonary *S. aureus* challenge is given and 4 h later the lungs are harvested to quantitatively culture for *S. aureus*. Also, a culture independent approach is used that provides information about the relative contributions of bacterial killing and clearance. DNA from “dead” vs. “live” bacteria can be distinguished by treating samples with DNase I prior to PCR with *S. aureus*-specific 16S primers. “Live” bacterial DNA is resistant to DNase I treatment, while “dead” (extracellular) DNA is DNase I sensitive (FIG. 17). For example, if THAM corrects the bacterial killing defect but not clearance one would expect to see a reduction of live bacteria DNA, with no difference in the total *S. aureus* DNA. This assay allows the ability to correlate over time ASL pH to eradication of *S. aureus*, and provides information about the relative contribution of bacterial killing and clearance.

Approach #2: Endogenous lung bacteria. Within 6-12 h after birth, CF pig lungs have more bacteria than non-CF. It is determined if THAM decreases the number of live bacteria in CF lungs. Within 4 h of vaginal birth, piglets (n=8/group) receive THAM or control treatment. Animals are euthanized (4 h later), lungs sterilely removed, and the lungs and BAL is used for bacterial analysis of culturable and nonculturable bacteria. For non-culturable bacteria, DNA-based microbial analysis is used for total bacterial DNA load and bacterial diversity (16S rRNA sequencing, ±DNase I) (FIG. 17). This assay measures THAM’s effects on both killing and clearance of endogenous microbiota.

Approach #3: Bacteria-coated grids. ASL bacterial killing is determined with a novel grid assay that measures killing, independent of other airway host defenses, such as MCT or immune cells (FIG. 4A). In this assay, *S. aureus* or *P. aeruginosa* are attached to a gold grid to interrogate killing of individual immobilized bacteria, which can be directly measured using a live-dead stain. When the grid is briefly touched (typically 1 min) to the airway surface or exposed to ASL or sputum, endogenous antimicrobials rapidly kill bacteria. With this assay, it was found that aerosolized THAM acutely restored ASL bacterial killing in human CF sputum (FIG. 13B) and newborn CF pig airways. Bacterial killing is tested at the same time points as in Approach #1. This assay allows the ability to correlate ASL pH with bacterial killing over time.

Nasal Bacterial Colonization Patterns in Humans after Airway Alkalinization

Nasal swabs were obtained from subjects with CF and from healthy subjects. Nasal bacterial counts were stable over three days, and CF nasal swabs tended to have more culturable bacteria (FIG. 18A). Nasal swabs from all CF subjects (100%) grew either *S. aureus* or *P. aeruginosa*. In initial studies, these two organisms were not isolated from non-CF swabs although *S. aureus* can colonize the nose of non-CF subjects. 16S-rRNA sequencing was performed from two non-CF subjects. The nasal microbial composition, within a subject, was relatively constant over the time periods studied (FIG. 18B).

Prior work showed that aerosolized xylitol decreased nasal coagulase-negative *S. aureus* colonization in non-CF subjects. The present study is a randomized, double-blinded, cross-over study of THAM followed by saline or saline followed by THAM in human non-CF and CF subjects (n=16/group) (FIG. 19). Day(D) 1: Both anterior nares are cultured and nasal ASL collected. D1-4: Subjects spray each nostril with a prefilled syringe of THAM or saline three times/day. D5: Subjects spray the final application at breakfast, then a nasal swab, for microbiology and ASL collection is obtained 4 h later. No treatments for the next 14 days, except that nasal sampling is performed on D11 similar to D5 and to confirm drug washout. D18-21: Subjects repeat the protocol but with the opposite solution as D1-4. D22: Similar to D5. Outcomes: Cultures are obtained with sterile swabs for quantification and identification of all bacterial species using standard microbiology techniques (plating/MALDITOF) and 16S rRNA sequencing ±DNase I pretreatment. Nasal ASL is used for pH and bacterial killing assays.

Impact of Alkalinization with THAM on CF ASL Biophysical Properties

It has been found that sputum from people with CF, as well as mucus from newborn CF pigs and from primary cultures of CF human and pig airway epithelia, have increased viscosity, which could contribute to impaired MCT. It was found that an acidic ASL pH influences mucus electrostatic interactions and was necessary and sufficient for genotype-dependent viscosity differences. Other variables, such as $[HCO_3^-]$ (independent of pH) and increased percentage of nonvolatile material, were less important. Increasing ASL pH with THAM improves CF ASL viscoelastic properties.

Two approaches are used to investigate the viscoelastic properties of airway mucus. First, mucus is collected from tracheal windows in methacholine-stimulated non-CF and CF newborn piglets (n=6/genotype) and then THAM (4 μl) or control solution is mixed with mucus (10 μl). Single particle tracking and one-point passive microrheology is used to probe the mechanical properties of the mucin gel network. The method of passive microrheology employs the thermal motion (Brownian motion) of micron-sized tracer microspheres embedded in the material to extract $G^*(\omega)$. The complex shear modulus can be separated into its components, the elastic and viscous moduli, $G^*(\omega)=G'(\omega)+iG''(\omega)$. Elasticity measures the ability of mucus to resume its original shape after being stretched or compressed. Viscosity measures the ability of mucus to absorb and dampen shock impulses, similar to a dashpot. Initial experiments indicate that CF pig mucus has both increased elasticity and viscosity, compared to non-CF (FIG. 20). Second, in airway epithelial cell cultures from non-CF and CF newborn pig and human donors, mucus viscosity (±THAM) is estimated by measuring the diffusion of fluorescent FITC-dextran with a FRAP assay and ASL/mucus pH using the pH indicator SNARF-1 (FIG. 11D&13A). Viscosity is directly correlated to diffusion. If the viscosity is high, FITC-dextran will slowly diffuse to the photo-bleached ASL areas.

Airway Alkalinization Restores Mucociliary Transport in CF Pig Airways

Currently available therapeutics that target defective MCT are limited (i.e., dornase alpha and hypertonic saline), do not target the underlying mechanism (acidic ASL pH), and are less clinically effective in younger populations. There is an urgent need for new strategies to correct defective MCT. By restoring ASL pH, defective MCT is corrected in newborn CF pigs.

At 0, 1.5 h, and 6.5 h following THAM or control treatment (section 3.5), MCT (before and after methacholine stimulation) is measured by tracking the movement of individual radiopaque microdisks in the airways of sedated, spontaneously breathing non-CF and CF newborn pigs (n=8/group). Individual and average microdisk velocities and heterogeneity measurements (mean, maximal, fastest microdisk, % moving microdisks, transient microdisk acceleration, velocity variations, and correlations of velocity and airway tree location) are measured.

Effects of Airway Alkalinization on Early Airway Disease in CF Pigs

Many infants with CF have airway infection and inflammation within weeks to months of birth. Despite aggressive antibiotic therapy, early infections still occur and are associated with worse disease. Antibiotics primarily affect airway infection, while inhaled mucolytics primarily target airway mucus. Besides ivacaftor (the CFTR potentiator approved for ~4-5% of CF population), and the combination lumacaftor-ivacaftor (which has limited clinical benefit), there are no CF therapies that potentially target abnormal ASL pH. More effective therapeutic solutions and targeted approaches are desperately needed to impact early CF airway disease and long-term outcomes.

CF pigs develop lung and sinus disease within weeks to months of birth. A study was recently completed that investigated disease development over the first 3 weeks of life. CFTR−/− pigs were used that are transgenic for porcine CFTR cDNA driven by an intestinal fatty acid-binding protein (FABP) promoter (CF-FABP, gut-corrected CF pigs). CF-FABP pigs lack meconium ileus, but develop airway disease similar to CF pigs that had meconium ileus corrected surgically. At 3 weeks of age, CF pigs had: 1) more lung bacteria (FIG. 21A); 2) histological evidence of CF lung disease (FIG. 21B); 3) more air trapping, consistent with airflow obstruction (FIG. 21C); and 4) sinusitis (FIGS. 22A-D). Thus, it is possible to investigate very early time points in CF. Correction of ASL pH with inhaled THAM restores host defense thereby preventing and/or alleviating airway disease in CF pigs.

CF-FABP pigs are used as subject animals, and WT pigs are used as controls. Study design. Non-CF and CF; control or THAM inhalation. n=8/group. THAM nebulization begins within 12-24 h of birth because 1) airway host defense defects are already present; and 2) CF pig lungs already have more bacteria. Thrice daily nebulizations continue for 3 weeks and then the animals are studied.

Endpoints/Assays.

Lung bacteria. The lung is sterilely sampled (3 tissue pieces/lobe) and BAL (2 regions) is performed to quantify culturable and non-culturable bacteria. Lung/sinus histology scoring. Randomized fields of view distributed over three sections per lung lobe are obtained based upon ATS/ERS guidelines. Histology is scored: airway inflammation (0-3), airway obstruction (0-3), and mucus accumulation (0-3). Analyses are performed on individual scoring components and a total composite disease score are determined (0-9). Chest/sinus CT-imaging. Using volumetric chest CT scanning, air trapping, lung volumes, airway size/wall thickening, mucus plugging, and parenchymal changes are quantified. Sinus CT scans are used to measure sinus mucosal wall thickening, growth, and plugging. Bronchoalveolar lavage (BAL) cell counts, cytokines, and airway mRNA. Cell count and cytokine analyses are performed. Airway/lung tissue is obtained for RNA/protein analysis. MCT assay. A separate cohort of animals are used since IV methacholine is used for the assay. Prior to euthanasia, animals undergo CT-based MCT assessment (before/after methacholine). Electrophysiology. Excised trachea/bronchi are studied. Host defense assays. Both in vivo (at study conclusion) and using airway epithelial cultures from these animals, ASL pH, bacterial killing, and viscosity are determined. Airway cultures. Trachea, bronchi, and sinus tissues are used for primary air-liquid interface cultures for above assays. Safety assessment. hematology, clinical chemistry, urinalysis studies, a complete necropsy, and detailed histological analysis are performed.

Although the foregoing specification and examples fully disclose and enable the present invention, they are not intended to limit the scope of the invention, which is defined by the claims appended hereto.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms “a” and “an” and “the” and similar referents in the context of describing the invention are to be construed to cover both the singular and the plural, unless otherwise indicated herein or clearly contradicted by context. The terms “comprising,” “having,” “including,” and “containing” are to be construed as open-ended terms (i.e., meaning “including, but not limited to”) unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., “such as”) provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of treating an airway infection in a mammal in need thereof by administering a therapeutically effective amount of a therapeutic composition consisting of tromethamine, an effective amount of hypertonic saline and an effective amount of $NaHCO_3$.

2. The method of claim 1, wherein $NaHCO_3$ is present at a concentration of about 1% to about 10%.

3. The method of claim 1, wherein the tromethamine is at a concentration of about 0.36 g/l to about 200 g/l.

4. The method of claim 1, wherein the hypertonic saline comprises NaCl at a concentration of about 7%.

5. The method of claim 1, wherein the therapeutic composition is administered orally, by aerosol inhalation, dry powder inhalation, liquid inhalation, liquid instillation, bronchoscopic instillation, nasal lavage or sinus lavage.

6. The method of claim 1, wherein the tromethamine is at a concentration of 0.3 M.

7. A method of treating an airway infection in a mammal in need thereof by administering a therapeutically effective amount of a therapeutic composition, wherein the therapeutic composition consists of tromethamine, tobramycin, and one or more agents selected from the group consisting of an effective amount of hypertonic saline and an effective amount of $NaHCO_3$.

8. The method of claim 7, wherein the therapeutic composition consists of tromethamine, an effective amount of hypertonic saline, an effective amount of $NaHCO_3$, and an effective amount of tobramycin.

9. The method of claim 7, wherein $NaHCO_3$ is present at a concentration of about 1% to about 10%.

10. The method of claim 7, wherein the therapeutic composition is administered orally, by aerosol inhalation, dry powder inhalation, liquid inhalation, liquid instillation, bronchoscopic instillation, nasal lavage or sinus lavage.

11. The method of claim 7, wherein the tromethamine is at a concentration of 0.3 M.

12. The method of claim 7, wherein hypertonic saline is present in the therapeutic composition, and the hypertonic saline comprises NaCl at a concentration of about 1% to about 8%.

13. The method of claim 7, wherein the tromethamine is at a concentration of about 0.36 g/l to about 200 g/l.

* * * * *